US012642465B2

(12) United States Patent
Carse et al.

(10) Patent No.: US 12,642,465 B2
(45) Date of Patent: Jun. 2, 2026

(54) DEVICES AND SYSTEMS FOR AUTOMATED COLLECTION OF BLOOD INTO TUBE STORED AT ATMOSPHERIC PRESSURE

(71) Applicant: P5 DESIGNERS, LLC, Milford, NJ (US)

(72) Inventors: Paul D. Carse, Milford, NJ (US); Cordelia A. Ogren, Milford, NJ (US); Patrik Johansson, Sudbury, MA (US); Kelly Gail Duncan, Washington, NJ (US); William Carr, Phillipsburg, NJ (US); David Tavor, Hod Hasharon (IL); Matthew L. Norris, Manville, NJ (US)

(73) Assignee: P5 Designers, LLC, Milford, NJ (US)

( * ) Notice: Subject to any disclaimer, the term of this patent is extended or adjusted under 35 U.S.C. 154(b) by 538 days.

(21) Appl. No.: 18/022,388

(22) PCT Filed: Aug. 19, 2021

(86) PCT No.: PCT/IL2021/051021
§ 371 (c)(1),
(2) Date: Feb. 21, 2023

(87) PCT Pub. No.: WO2022/038616
PCT Pub. Date: Feb. 24, 2022

(65) Prior Publication Data
US 2023/0320637 A1 Oct. 12, 2023

Related U.S. Application Data

(60) Provisional application No. 63/068,392, filed on Aug. 21, 2020.

(51) Int. Cl.
A61B 5/15 (2006.01)
A61B 5/00 (2006.01)
(Continued)

(52) U.S. Cl.
CPC .... A61B 5/150099 (2013.01); A61B 5/15003 (2013.01); A61B 5/150221 (2013.01);
(Continued)

(58) Field of Classification Search
CPC .......... A61B 5/150099; A61B 5/15003; A61B 5/150221; A61B 5/150229; A61B 5/150351
See application file for complete search history.

(56) References Cited

U.S. PATENT DOCUMENTS 3,742,934 A 7/1973 Holbrook et al.
5,238,655 A 8/1993 Laible et al.
(Continued)

FOREIGN PATENT DOCUMENTS

CN 204618253 U 9/2015

OTHER PUBLICATIONS

PCT International Search Report and Written Opinion, PCT/IL2021/051021, Nov. 29, 2021, 14 pages.

*Primary Examiner* — Daniel L Cerioni
(74) *Attorney, Agent, or Firm* — Fenwick & West LLP

(57) ABSTRACT

A blood collection tube includes a body, a chamber, a vacuum port, and a cap. The cap includes a first septum, a first conduit having an inlet extending from the first septum and an outlet in fluid communication with the chamber, a second septum, and a second conduit extending radially from the second septum to the first conduit. When a fluid source is fluidically connected to the first septum or the second septum, and a vacuum is applied at the port, the vacuum draws fluid from the fluid source, through the first or second septum, and into the first conduit. A blood collection device includes a vacuum pump and a plurality of reservoirs containing concentrated blood additives. The tube and device form a system for collecting blood samples at (Continued)

low vacuum to tubes previously stored at atmospheric pressure. The system prevents risk of misidentification, mislabeling, or incorrect ordering of tubes.

24 Claims, 20 Drawing Sheets

(51) Int. Cl.
    *A61B 5/153*          (2006.01)
    *A61B 5/157*          (2006.01)
(52) U.S. Cl.
    CPC .. *A61B 5/150229* (2013.01); *A61B 5/150351*
            (2013.01); *A61B 5/150755* (2013.01); *A61B*
                *5/150786* (2013.01); *A61B 5/150847*
            (2013.01); *A61B 5/153* (2013.01); *A61B 5/157*
                (2013.01); *A61B 5/742* (2013.01)

(56) References Cited

U.S. PATENT DOCUMENTS

| | | | | |
|---|---|---|---|---|
| 5,474,544 | A * | 12/1995 | Lynn ..................... | A61M 39/02 |
| | | | | 604/537 |
| 6,224,561 | B1 * | 5/2001 | Swendson ........ | A61B 5/150992 |
| | | | | 600/562 |
| 6,342,048 | B1 | 1/2002 | Verkaart et al. | |
| 2008/0091173 | A1 * | 4/2008 | Belley .............. | A61M 25/0606 |
| | | | | 604/537 |
| 2019/0053747 | A1 | 2/2019 | Lapidus et al. | |
| 2021/0137436 | A1 * | 5/2021 | Burkholz ......... | A61B 5/150992 |
| 2021/0220548 | A1 * | 7/2021 | Kimball .............. | A61M 39/221 |

* cited by examiner

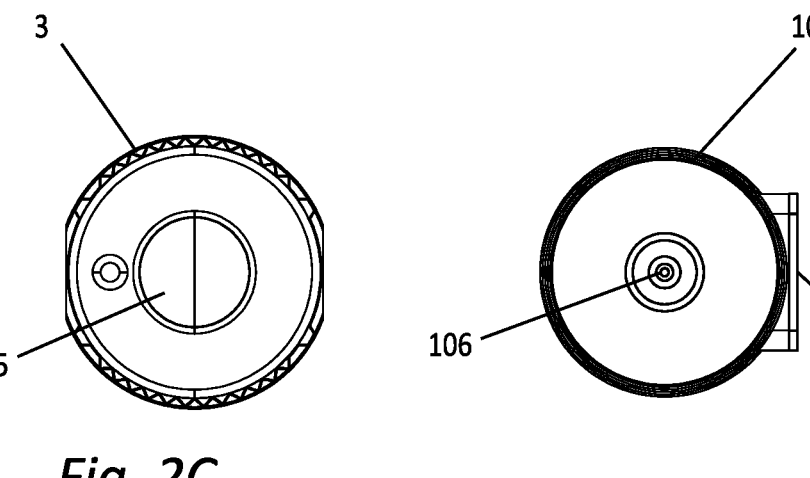
*Fig. 2C*
*Prior Art*
*Fig. 2D*
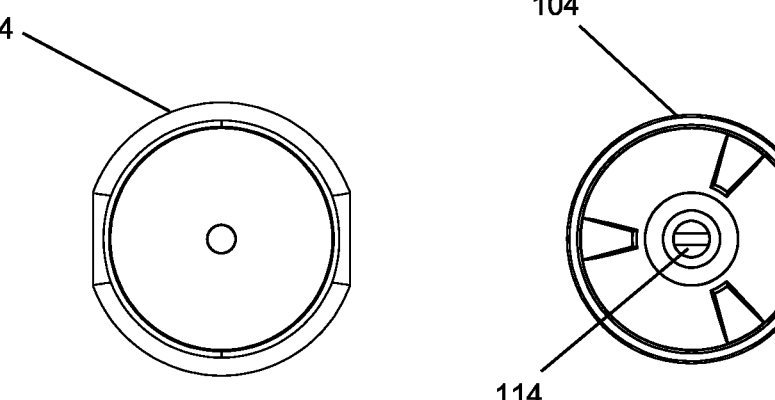
*Fig. 2E*
*Prior Art*
*Fig. 2F*

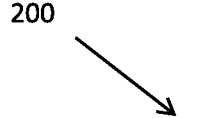
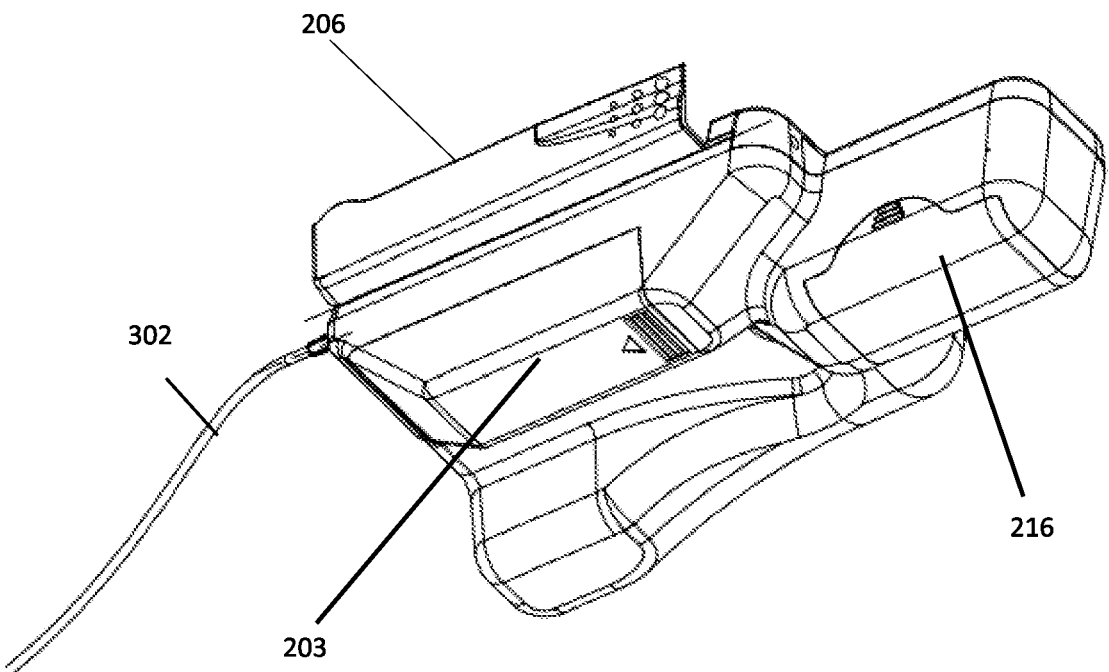
*Fig. 8C*

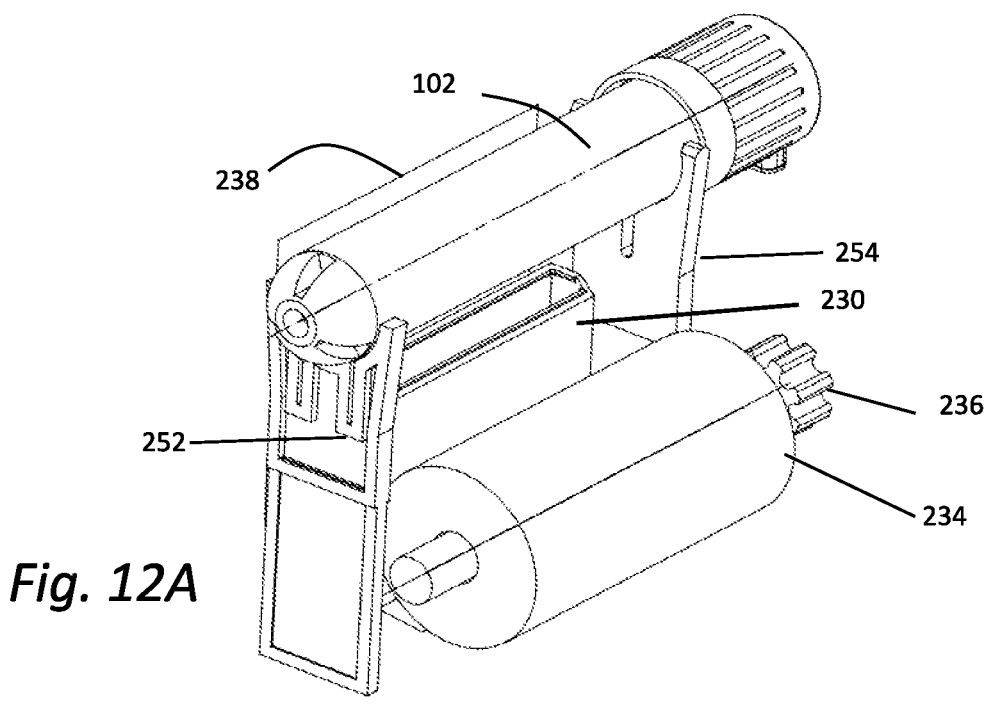
*Fig. 12A*
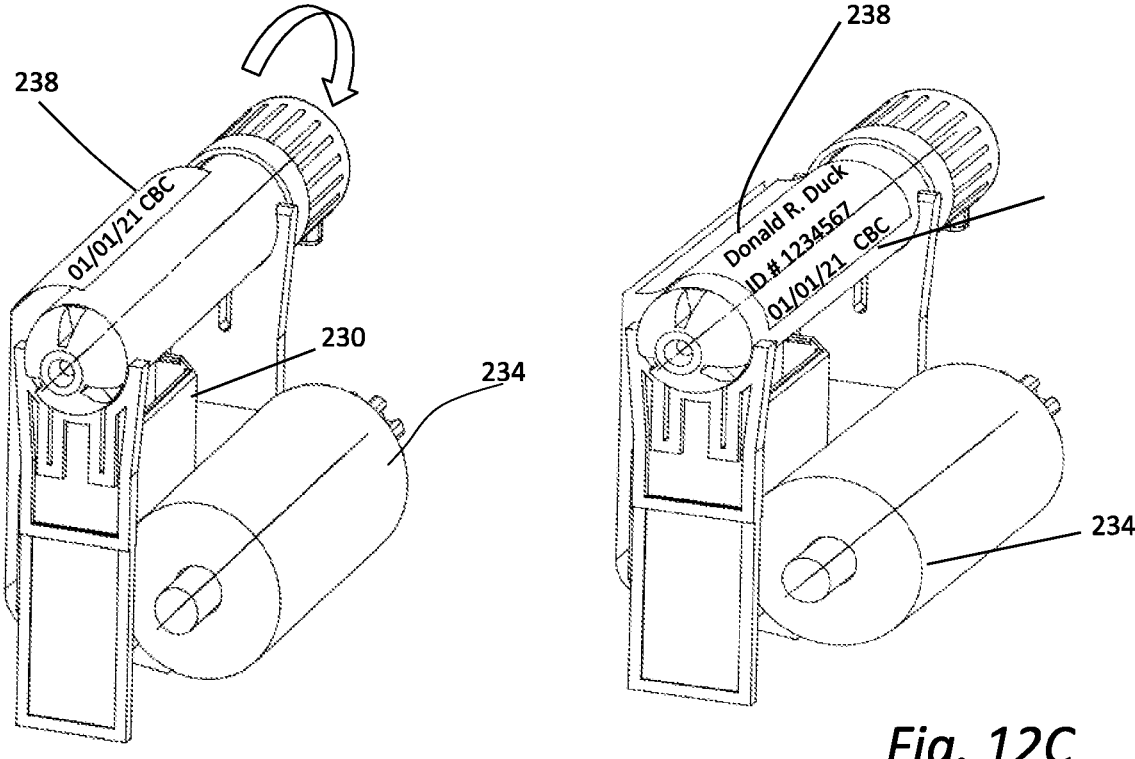
*Fig. 12B*
*Fig. 12C*

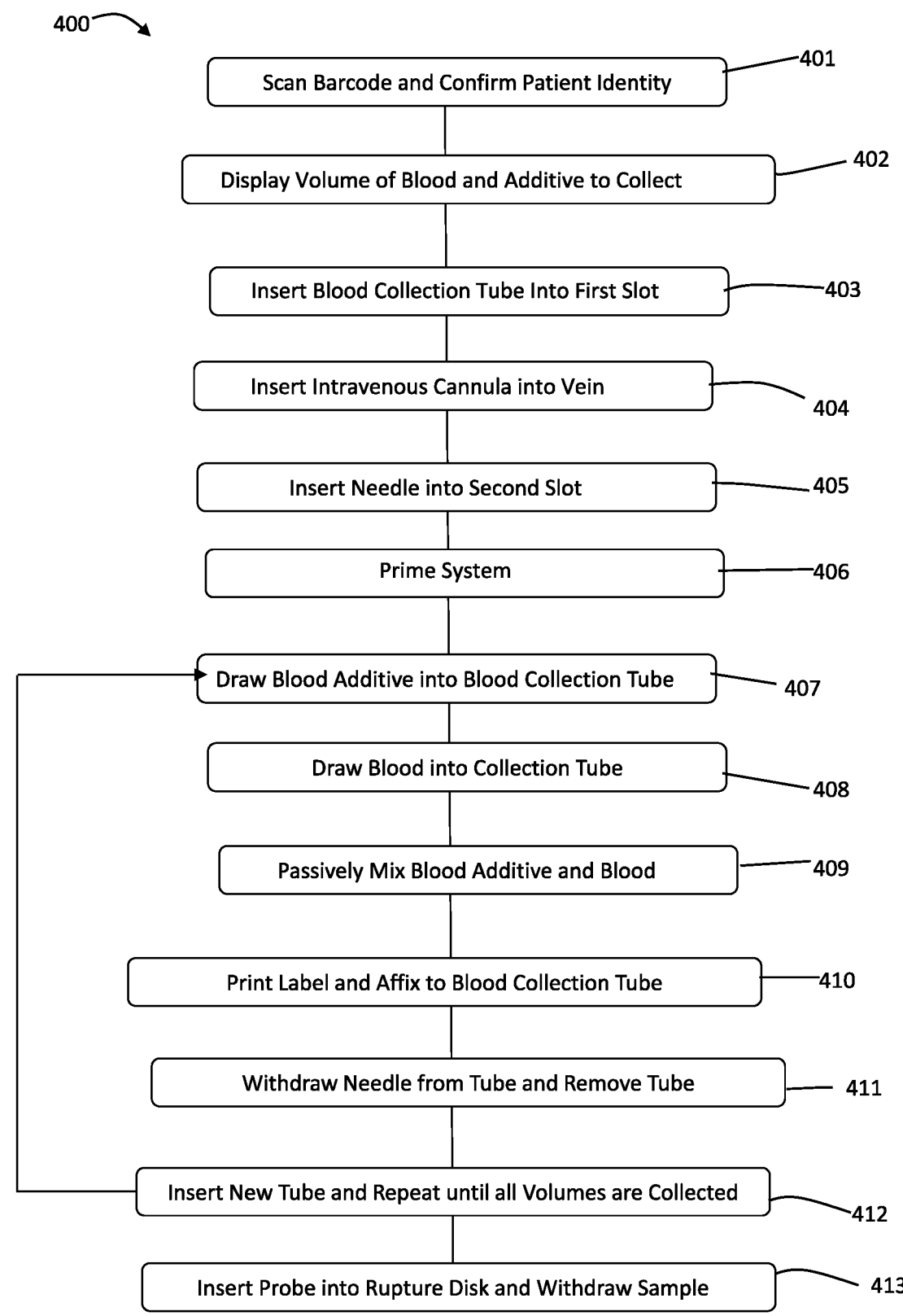

400

Scan Barcode and Confirm Patient Identity ——401

Display Volume of Blood and Additive to Collect ——402

Insert Blood Collection Tube Into First Slot ——403

Insert Intravenous Cannula into Vein ——404

Insert Needle into Second Slot ——405

Prime System ——406

Draw Blood Additive into Blood Collection Tube —— 407

Draw Blood into Collection Tube ——408

Passively Mix Blood Additive and Blood ——409

Print Label and Affix to Blood Collection Tube ——410

Withdraw Needle from Tube and Remove Tube —— 411

Insert New Tube and Repeat until all Volumes are Collected ——412

Insert Probe into Rupture Disk and Withdraw Sample —— 413

| Analyte | 419, C Control | 419, 1 12 uL | 419,2 10 uL | 419,3 8 uL |
|---|---|---|---|---|
| WBC | 7.6 | 7.6 | 7.7 | 7.4 |
| RBC | 4.60 | 4.60 | 4.68 | 4.68 |
| HGB | 14.3 | 14.5 | 14.5 | 14.4 |
| HCT | 43.3 | 43.2 | 43.7 | 43.3 |
| MCV | 94.1 | 93.9 | 93.4 | 92.5 |
| MCH | 31.1 | 31.5 | 31.0 | 30.8 |
| MCHC | 33.0 | 33.6 | 33.2 | 33.3 |
| RDW | 12.9 | 12.6 | 12.8 | 12.7 |
| PLT | 275 | 268 | 287 | 264 |
| MPV | 10.3 | 10.6 | 10.7 | 10.5 |
| NEUT | 57.3 | 57.0 | 55.7 | 55.0 |
| LYMPH | 35.6 | 35.1 | 36.4 | 37.3 |
| MONO | 6.1 | 6.9 | 6.8 | 6.5 |

*Fig. 15A*

| Analyte | 419, C Control | 419, 1 36 uL | 419,2 30 uL | 419,3 24 uL |
|---|---|---|---|---|
| GLU | 121 | 123 | 126 | 128 |
| BUN | 16 | 16 | 16 | 15 |
| CREA | 0.84 | 0.79 | 0.80 | 0.75 |
| NA | 139 | 135 | 136 | 136 |
| K | 3.7 | 4.0 | 4.0 | 4.0 |
| CL | 102 | 100 | 100 | 101 |
| CO2 | 24 | 26 | 25 | 25 |
| CA | 9.7 | 9.2 | 9.2 | 9.1 |
| TP | 7.1 | 6.9 | 6.8 | 6.7 |
| ALB | 4.3 | 3.6 | 3.7 | 3.6 |
| TBIL | 0.4 | 0.4 | 0.4 | 0.4 |
| ALKP | 57 | 51 | 52 | 51 |
| AST | 17 | 17 | 17 | 17 |
| ALT | 8 | 6 | 6 | 8 |

*Fig. 15B*

DEVICES AND SYSTEMS FOR AUTOMATED COLLECTION OF BLOOD INTO TUBE STORED AT ATMOSPHERIC PRESSURE

RELATED APPLICATIONS

This Application claims priority to U.S. Provisional Patent Application 63/068,392, entitled "Automated Micro Collection Device," filed Aug. 21, 2020, the contents of which are incorporated by reference as if fully set forth herein.

FIELD OF THE INVENTION

The present Application relates to the collection of blood into blood collection tubes for testing, and more specifically, but not exclusively, to a blood collection tube, blood collection device, and method for collecting blood into tubes that are stored at atmospheric pressure.

BACKGROUND OF THE INVENTION

Analysis of blood samples is one of the most important diagnostic tools available for the detection and treatment of diseases. Blood samples are obtained by a process known as venipuncture. During venipuncture, a cannula is inserted into a vein, and blood is drawn through tubing attached to the cannula into one or more blood collection tubes. The blood collection tubes may have one or more additives for preventing coagulation or for isolating certain components of the blood.

For over 70 years, the industry standard for blood collection tubes has been the evacuated blood collection tube, such as the Vacutainer® manufactured by Becton Dickinson. An evacuated blood collection tube is prepared by adding a blood additive into the tube, stoppering the tube, applying a vacuum to the tube, and storing the tube maintained at internal vacuum conditions. Evacuated blood collection tubes account for nearly 1% of global medical supply sales, and it is estimated that annual global sales of evacuated blood collection tubes exceed $1.7 billion.

An exemplary prior art evacuated blood collection tube is displayed in FIGS. 1A, 2A, 2C, 2E, and 3A. Blood collection tube 1 includes body 2, cap 3, and curved bottom 4. Cap 3 may be color coded in order to indicate the type of additive that is within body 2. Aside from the volume taken by the additive, substantially the entire interior of the body 2 is available for storing a blood sample.

Blood collection tubes 1 typically come in standard sizes and volumes. For example, a standard 3 ml tube is 75 mm long and has a diameter of 13 mm. Other standard sizes include a diameter of 16 mm and length of 100 mm.

A septum 5 is configured within the cap 3. The septum 5 is sufficiently strong to maintain a vacuum within tube 1 for the shelf life of the tube 1, which may be months or years. During collection of a blood sample, a phlebotomist inserts a needle connected to an intravenous cannula through the stopper, and the evacuated tube draws in a volume of blood. Following the collection, the phlebotomist inverts tube up to ten times, in order to mix the additive(s) and the blood thoroughly.

SUMMARY OF THE INVENTION

Despite their widespread use, evacuated blood collection tubes pose numerous challenges. First, the evacuated blood collection tube must be evacuated to a relatively high vacuum pressure. This high vacuum pressure causes the blood to enter the tube with force, which may cause hemolysis of the red blood cells, thereby requiring a repeat blood collection. In addition, the high vacuum pressure may be painful to a patient, especially a patient with fragile veins. Moreover, maintaining the tubes at this negative pressure introduces costs associated with the evacuation process, and leads to waste due to expiration of the blood collection tubes when they lose their vacuums.

As a second challenge of evacuated blood collection tubes, use of evacuated blood collection tubes requires storage and tracking of up to nine different stock-keeping-units (SKUs), one for each different type of additive that is coated into the tube. This tracking increases the administrative burden of a facility performing blood sampling.

Still another challenge of evacuated blood collection tubes is that the vacuum in evacuated blood collection tubes is configured to collect a relatively large blood sample, consisting of several milliliters. This volume is much more than is needed for most standard assays. Collection of excessive blood may increase patient pain, and at times compromises patient safety. However, the technology of evacuated blood collection tubes does not allow for tailoring of the collected volumes to specific assays. Once an additive is added to a blood collection tube, it is necessary to collect an essentially fixed volume of blood, so that the ratio of blood to additive is within desired parameters.

Finally, the use of evacuated blood collection tubes is highly prone to human error, especially in a hospital setting. Human error may arise from numerous sources. First, it is necessary to draw blood in a particular sequence of tubes, each having a different additive. Drawing blood in the wrong order may cause contamination of later-collected tubes, thereby requiring re-drawing of the contaminated blood samples. Second, in a hospital setting, a phlebotomist travels from bed to bed, collecting blood from a list of patients. The phlebotomist is tasked with keeping track of which patients to collect blood from, and which types of tubes to collect from each patient, often based solely on a printed list. The risk of error is evident.

Cumulatively, the costs arising from errors in blood collection is staggering. According to one recent study, an average-sized U.S. hospital processes 182,500 blood collection tubes per year. Of those, 0.66% have errors due to mislabeling, insufficient quantity of collected blood (often caused by used of expired tubes), or wrong tube usage. 72% of such errors lead to additional patient-treatment costs. The average cost of such pre-analytical errors is $208; thus, cumulatively, the errors amount to approximately $180,000 in additional cost per year, just for that single hospital. Beyond the costs of additional tubes and laboratory processing, the largest cost associated with such errors is in patient care. The delays in obtaining accurate blood testing cause delays in diagnosis and treatment, which may, in turn, lead to complications in a patient's condition.

In addition, it is impossible to implement an extremely low vacuum in evacuated vacuum tubes that are known, because the vacuum would not typically last a sufficiently long time, from manufacture to use of the tubes, to be practically useful.

Accordingly, there is a need to develop a blood collection system that does not rely on evacuated blood collection tubes. There is a further need to develop a blood collection system that is capable of using the a standard blood collection tube for all blood collections, regardless of the different additives that are to be mixed with the blood. There is a further need for a blood collection system that is able to collect the minimum amount of blood required for testing. There is a further need to develop a blood collection system that reduces the potential for human error in the collection of blood samples, whether in misidentification of patients or in collecting blood samples in the wrong order, or in labeling errors.

The present disclosure presents a blood collection system that addresses each of these objectives. A blood collection tube has a first septum for input of blood, a second septum for input of a blood additive, and vacuum port. A blood collection device includes a vacuum pump and a plurality of reservoirs containing concentrated blood additives. When the blood collection tube is inserted into the blood collection device, the vacuum pump applies a vacuum through the vacuum port. The applied vacuum draws into the blood collection tube both an aliquot of the concentrated blood additive, and a predefined volume of blood. The blood additive and blood are then mixed in the blood collection tube, optionally in a passive mixing labyrinth. Prior to the collection, the phlebotomist confirms patient identity and order of blood collection tubes with a processor built in to the blood collection device. The blood collection is performed at low vacuum, and draws the minimum required quantity of blood, with virtually no risk of misidentification of patients, incorrect ordering of collection tubes, or mislabeling of specimens.

According to a first aspect, a blood collection tube is disclosed. The tube includes a body including a proximal end and a distal end, and defining an axial extent between the proximal end and the distal end. The tube further includes a chamber within the body, a vacuum port, and a cap arranged on the proximal end. The cap includes a top face including a first septum, a first conduit having an inlet extending from the first septum and an outlet in fluid communication with the chamber, a lateral face including a second septum, and a second conduit extending radially from the second septum to the first conduit. When a fluid source is fluidically connected to the first septum or the second septum, and a vacuum is applied at the vacuum port, the vacuum draws fluid from the fluid source, through the first or second septum, and into the first conduit.

In another implementation according to the first aspect, a passive mixing labyrinth is arranged between the outlet of the first conduit and the chamber. Optionally, the passive mixing labyrinth is configured to mix fluid passing therethrough at least ten times before delivering the liquid to the chamber. Optionally, the passive mixing labyrinth comprises both lateral turns and axial turns. Optionally, the passive mixing labyrinth comprises a rupture disc axially aligned with the first conduit and the first septum.

In another implementation according to the first aspect, the chamber has a funnel-shaped geometry including a substantially conical portion at a proximal end thereof and a substantially cylindrical portion at a distal end thereof. Optionally, an internal volume of the chamber is approximately 1 ml, and a volume of the tube is approximately between 3 ml and 5 ml.

In another implementation according to the first aspect, a membrane is configured between the vacuum port and the chamber, said membrane configured to permit vacuum to be drawn therethrough but being non-permeable to liquid. Optionally, a one-way valve is arranged between a distal end of the chamber and the membrane. The one-way valve is configured to sequester collected fluid coming into contact with the membrane from fluid remaining in the chamber.

In another implementation according to the first aspect, an axial length of the tube is between approximately 75 and 100 mm, and a diameter of the cap is between approximately 13 and 16 mm.

According to a second aspect, a device for collecting blood into a blood collection tube is disclosed. The device includes a first slot for securing a blood collection tube therein; a vacuum pump; a second slot for securing a needle therein; a plurality of conduits, each conduit connected at a distal end thereof to a reservoir; and a processor configured to specify a predetermined volume of additive to be delivered into a blood collection tube from one of the plurality of reservoirs and a predetermined volume of blood to be delivered into the blood collection tube via the needle. The vacuum pump, plurality of conduits, and second slot are arranged around the first slot such that when a blood collection tube having a vacuum port, first septum, and second septum is inserted into the first slot: the vacuum pump is configured to draw a vacuum through the vacuum port; each conduit is fluidically connectable to an interior of the blood collection tube via the second septum; and a needle secured within the second slot is fluidically connectable to an interior of the blood collection tube via the first septum; and the processor is configured to control a vacuum delivered from the vacuum pump so as to draw the predetermined volumes of additive and blood into the blood collection tube.

In another implementation according to the second aspect, each conduit includes a needle that is separately insertable into and removable from the second septum. Optionally, the device includes a screw conveyor system for delivering each respective additive from a respective reservoir to the second septum, and each needle is a tip of a respective screw conveyor.

In another implementation according to the second aspect, a valve is configured between each conduit and respective reservoir, and a sensor array is configured to monitor flow of additive through each valve. Upon receipt of input specifying a volume of additive to be delivered from a particular reservoir, the processor directs opening of a corresponding valve, and when the sensor array senses that a specified volume of additive has entered the conduit from the reservoir, the processor directs closure of the corresponding valve.

In another implementation according to the second aspect, the second slot comprises a locking slot for securing the needle in the first septum. Optionally, a sensor is arranged at the locking slot and configured to sense locking of a needle into the locking slot. Optionally, upon sensing of locking of a needle into the locking slot, the processor initiates a self-priming process.

In another implementation according to the second aspect, a vacuum reservoir is configured to store a vacuum from the vacuum pump.

In another implementation according to the second aspect, the device includes a plurality of adhesive labels, a printer arranged to print on the plurality of adhesive labels, and a roller configured to rotate the blood collection tube within the first slot in order to apply a printed label onto an exterior of the blood collection tube.

In another implementation according to the second aspect, the device includes a screen, wherein the processor is configured to display on the screen information regarding an identity of the patient from whom blood is to be collected, a volume of additive to add to the blood collection tube, and a quantity of blood to collect in the blood collection tube.

In another implementation according to the second aspect, the device includes a scanner for scanning a bar code encoding patient information, and a memory containing stored patient information, wherein the processor is configured to permit collection of blood only when scanned encoded information matches the stored patient information.

In another implementation according to the second aspect a wireless transceiver configured to wirelessly receive and transmit the stored patient information.

In another implementation according to the second aspect, the device is handheld.

In another implementation according to the second aspect, a system for collecting blood includes the device and a blood collection tube. The blood collection tube includes a tube body including a proximal end and a distal end, and defining an axial extent between the proximal end and the distal end; a chamber within the tube body; a vacuum port; and a cap arranged on the proximal end, wherein the cap includes: a top face including a first septum; a first conduit having an inlet extending from the first septum and an outlet in fluid communication with the chamber; a lateral face including a second septum; and a second conduit extending radially from the second septum to the first conduit.

According to a third aspect, a method of collecting blood into a blood collection tube is disclosed. The method includes: drawing, with a vacuum, a volume of blood additive into a blood collection tube; and drawing, with a vacuum, a volume of blood into the blood collection tube.

In another implementation according to the third aspect, prior to the drawing steps, the blood collection tube is maintained at atmospheric pressure.

In another implementation according to the third aspect, the method further includes performing the first drawing step by applying a vacuum to the blood collection tube while the a cap of the blood collection tube is fluidically connected to a reservoir containing the blood additive, and performing the second drawing step by applying a vacuum to the blood collection tube while a cap of the blood collection tube is fluidically connected to an intravenous cannula.

In another implementation according to the third aspect, the method further includes selecting predetermined volumes of blood and a blood additive to draw into the blood collection tube, and controlling the applied vacuum so as to draw the predetermined volume of blood and blood additive into the blood collection tube.

In another implementation according to the third aspect, the method further includes passively mixing the volume of blood additive and volume of blood. The passively mixing step includes drawing the blood and the additive through a passive mixing labyrinth arranged within the blood collection tube. Optionally, the passively mixing step includes mixing the blood and additive within the passive mixing labyrinth at least ten times.

In another implementation according to the third aspect, the method further includes scanning a bar code associated with a patient, determining patient information based on the scanned bar code, comparing the determined patient information to stored patient information, and performing the drawing steps only when the determined patient information matches the stored patient information.

In another implementation according to the third aspect, the second drawing step includes drawing between 300 µl and 10 ml of blood into the blood collection tube.

In another implementation according to the third aspect, the method further includes printing a label for the blood collection tube, and affixing the label to the blood collection tube by automatically rotating the blood collection tube.

In another implementation according to the third aspect, the blood collection tube includes a chamber having a funnel-shaped geometry, the funnel-shaped chamber having a substantially conical proximal end and a substantially cylindrical distal end, and the method further comprises inserting a probe into the substantially conical proximal end, and withdrawing a sample of blood. Optionally, the method further includes inserting the probe into a rupture disk within a passive mixing labyrinth, and withdrawing the sample while the probe has penetrated the rupture disk.

In another implementation according to the third aspect, the blood collection tube includes a tube body including a proximal end and a distal end, and defining an axial extent between the proximal end and the distal end; a chamber within the tube body; a vacuum port; and a cap arranged on the proximal end, wherein the cap comprises: a top face including a first septum; a first conduit having an inlet extending from the first septum and an outlet in fluid communication with the chamber; a lateral face including a second septum; and a second conduit extending radially from the second septum to the first conduit; the first drawing step comprises drawing the volume of blood additive via the second septum through the second conduit; and the second drawing step comprises drawing the blood via the first septum through the first conduit.

Optionally, the method further includes piercing the first septum with a needle fluidically connected to an intravenous cannula.

Optionally, the method further includes inserting the blood collection tube into a first slot of a blood collection device, the blood collection device further comprising a vacuum pump, a second slot for securing a needle therein, said needle fluidically connected to an intravenous cannula, and a plurality of conduits, each conduit connected at a distal end thereof to a liquid reservoir. The vacuum pump, plurality of conduits, and second slot are arranged around the first slot such that, following the step of inserting the blood collection tube into the first slot: the vacuum pump is configured to draw a vacuum through the vacuum port; each conduit is fluidically connectable to an interior of the blood collection tube via the second septum; and the needle secured within the second slot is fluidically connectable to an interior of the blood collection tube via the first septum. The method further comprises performing the first drawing step and second drawing step by drawing the vacuum with the vacuum pump.

BRIEF DESCRIPTION OF THE DRAWINGS

In the drawings:

FIG. 2C is a top view of the prior art blood collection tube of FIG. 1A;

FIG. 2D is a top view of the blood collection tube of FIG. 1B, according to embodiments of the present disclosure;

FIG. 2E is a bottom view of the prior art blood collection tube of FIG. 1A;

FIG. 2F is a bottom view of the blood collection tube of FIG. 1B, according to embodiments of the present disclosure;

FIG. 8C is a lower perspective view of the blood collection device of FIG. 8A, according to embodiments of the present disclosure;

FIG. 12A is a perspective view of a printer and label generator within the blood collection device of FIG. 8A, according to embodiments of the present disclosure;

FIGS. 12B and 12C illustrate affixation of a printed label onto a blood collection tube, according to embodiments of the present disclosure;

FIG. 13 depicts steps of a method of collecting blood, according to embodiments of the present disclosure;

FIGS. 15A-B illustrate experimental results of blood counts obtained with different volumes of blood additives mixed with the same volume of blood, according to embodiments of the present disclosure.

DETAILED DESCRIPTION OF THE INVENTION

Figures 1A, 1B:
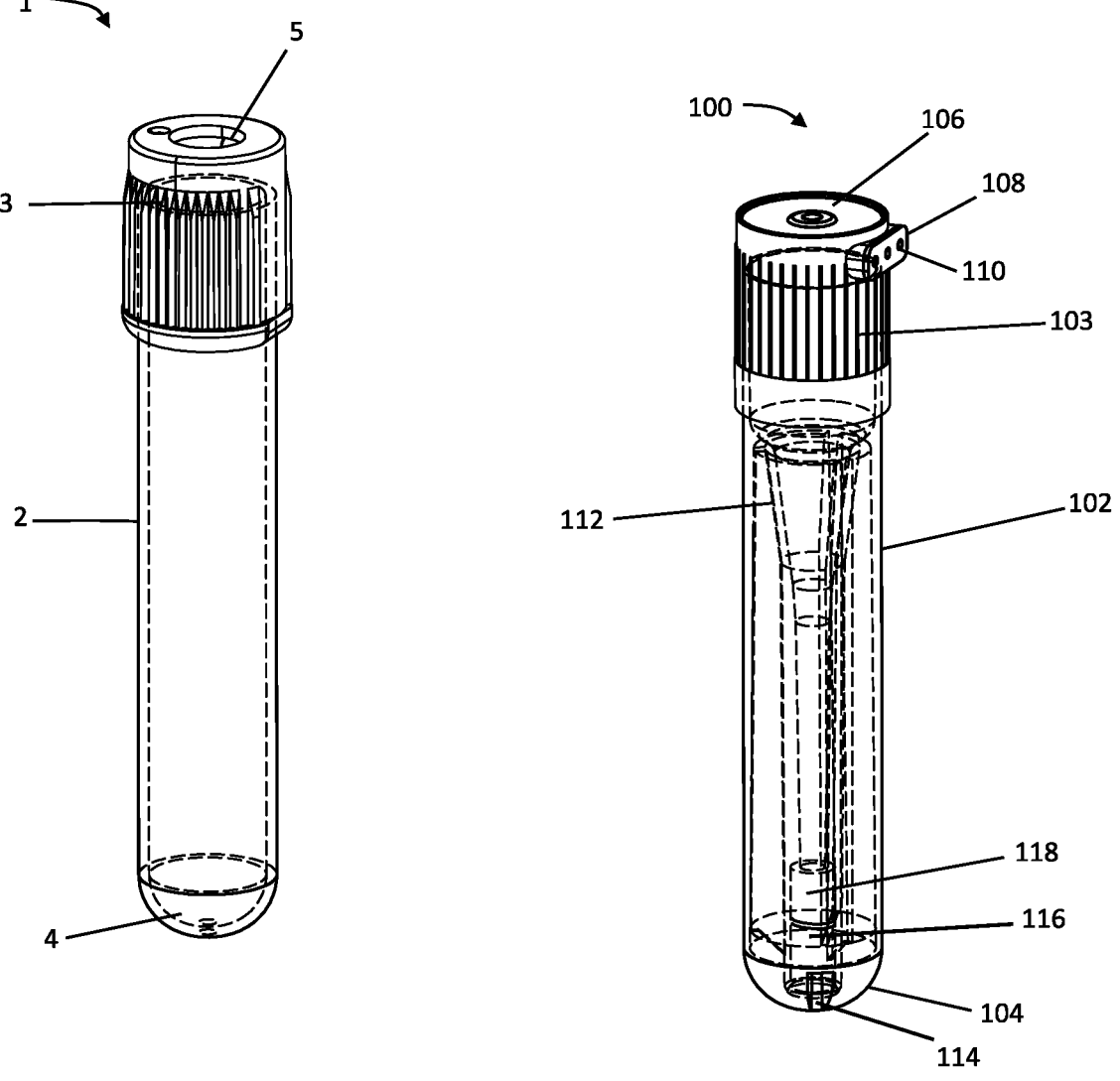
FIG. 1A is an isometric view of a prior art blood collection tube.
FIG. 1B is an isometric view of a blood collection tube, according to embodiments of the present disclosure.
Figure 2A:
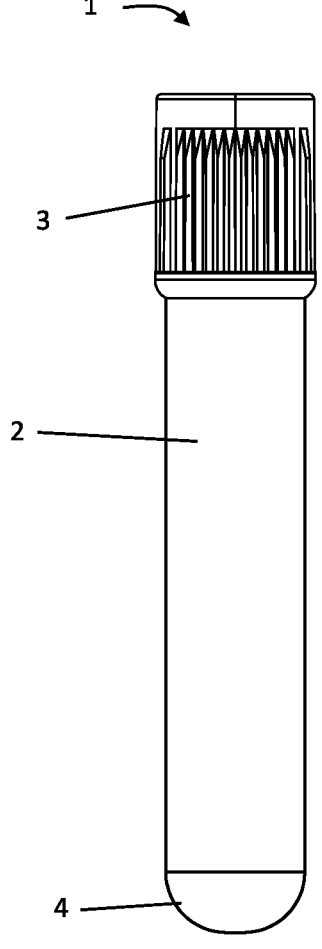
FIG. 2A is a side view of the prior art blood collection tube of FIG. 1A.
Figure 2B:
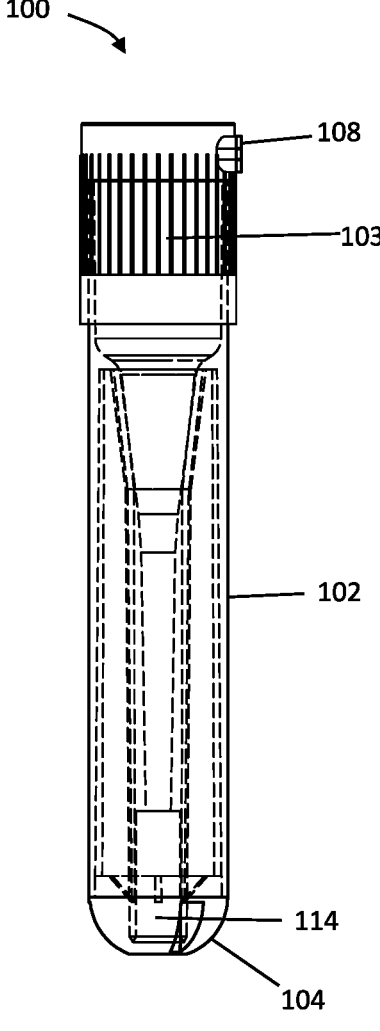
FIG. 2B is a side view of the blood collection tube of FIG. 1B, according to embodiments of the present disclosure.

The present Application relates to the collection of blood for testing, and more specifically, but not exclusively, to a blood collection tube, blood collection device, and method for collecting volumes of blood into collection tubes that are stored at atmospheric pressure.

Before explaining at least one embodiment in detail, it is to be understood that the invention is not necessarily limited in its application to the details of construction and the arrangement of components and/or methods set forth in the following description and/or illustrated in the drawings. The invention is capable of other embodiments or of being practiced or carried out in various ways.

FIGS. 1B, 2B, 2D, 2F, and 3B illustrate blood collection tube 100, according to embodiments of the present disclosure. Blood collection tube 100 includes body 102 defining a chamber therein, and a cap 103. Body 102 defines a proximal end, at cap 103, a distal end, at the bottom of the body 102, and an axial extent therebetween.

In preferred embodiments, the outer dimensions of body 102 and cap 103 are geometrically identical to those of prior art tube 1, body 2, and cap 3. For example, the axial length of tube 100 may be 75 mm and the diameter of the cap 103 may be 13 mm. Advantageously, tube 100 is accordingly compatible with existing equipment for storing blood collection tubes and for sampling blood collected in blood collection tubes. In addition, a technician using tube 100 will be comfortable with its shape and size.

Body 102 includes chamber 112 having a funnel-shaped geometry, which defines the contours of the chamber 112. Chamber 112 includes a substantially conical upper portion, and a substantially cylindrical lower portion with a narrower diameter than the upper portion. The funnel-shaped chamber 112 is used in order to make the height of blood within chamber compatible with the height of blood in chambers of prior art tubes 1. Tube 100 is designed to collect volumes of between 300 μl and 1 ml, whereas prior art tube 1 is designed to collect between 3 and 5 ml. Without a funnel-shaped geometry, blood collected in tube 100 would pool at the very bottom of body 102, causing difficulty in accessing the collected blood for analysis. For this reason, funnel-shaped chamber 112 limits the effective volume of the blood collection tube 100, and also ensures that the collected blood is accessible at an equivalent height compared to blood collected in tube 1.

It should be noted that, while the structure of tube 100 is particularly advantageous for collection of micro-volumes of blood, there is no technical impediment in the use of tube 100 for collection of larger volumes. For example, the volume of collected blood may be even as high as 10 ml, as in currently-used vacuum blood collection tubes. The shape of chamber 112 may be adjusted as needed in order to define a desired volume.

At a distal end of body 102 (i.e., at an end further from cap 103), tube 100 includes a vacuum port 114. Vacuum port 114 is a substantially cylindrical opening configured to interface with tubing from a vacuum pump, in order to draw a vacuum through chamber 112. In the illustrated embodiment; port 114 is at the distal end of body 102; in alternative embodiments, vacuum port 114 is configured along the axial extent of body 102. Between the vacuum port 114 and chamber 112 are liquid-impervious membrane 116 and valve 118, the functions of which will be described further herein.

Cap 103 is of a size and shape that are considered standard. Cap 103 consists of an outer shell with an over-molded or inserted septum 106 at a top face. Septum 106 is for receiving a needle carrying blood. Cap 103 further includes septum 108 at a lateral face, for receiving an injection of an aliquot of blood additive. Septum 108 optionally includes several defined holes or entry regions 110. Holes or entry regions 110 are locations in which the blood additive is inserted into the septum 108. In certain embodiments, holes 110 extend through the entire thickness of septum 108, and blood additives are drawn through holes 110 by a force of vacuum. In alternative embodiments, holes 110 are approximate locations where a needle may be inserted through septum 108, and the additives are inserted via a needle that is extended through the entire thickness of septum 108.

Figure 3A:
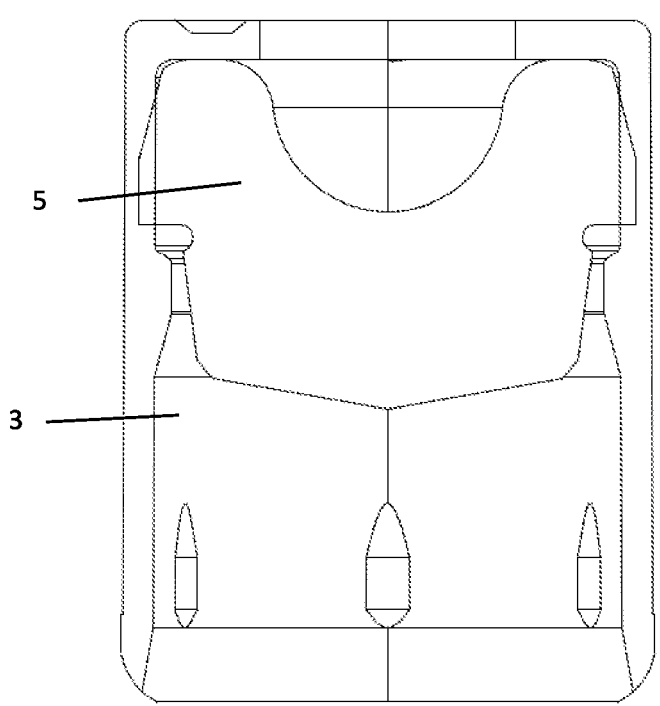
FIG. 3A is a cross section view of a cap of the prior art blood collection tube of FIG. 1A.
Figure 3B:
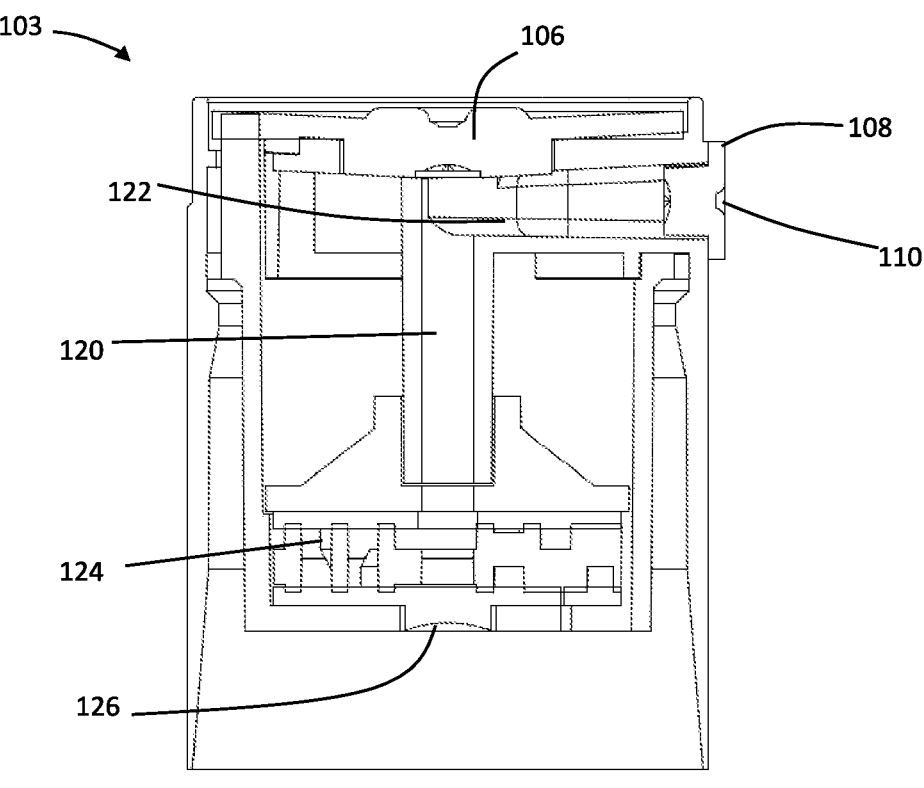
FIG. 3B is a cross section view of the cap of the blood collection tube of FIG. 1B, according to embodiments of the present disclosure.

Referring particularly to FIG. 3B, septum 106 is significantly thinner than an equivalent prior art septum 5 shown in FIG. 3A. Because tube 100 is not stored under vacuum, it is not necessary to have a thick septum therein to maintain a pressure differential within the chamber.

Figure 4A:
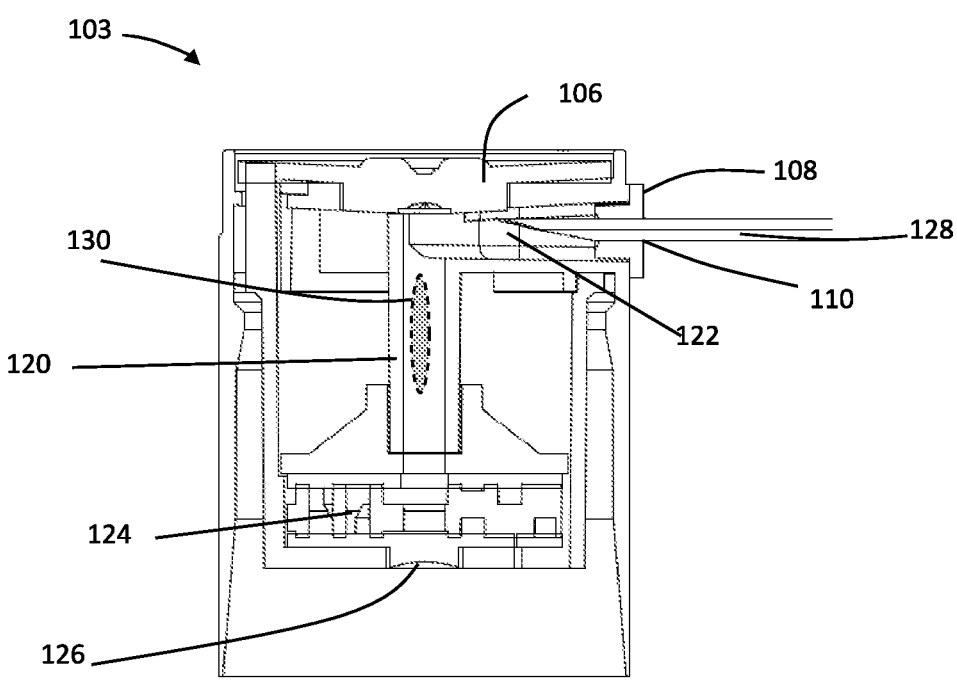
FIG. 4A illustrates a path of insertion of a blood additive into the blood collection tube of FIG. 1B, according to embodiments of the present disclosure.
Figure 4B:
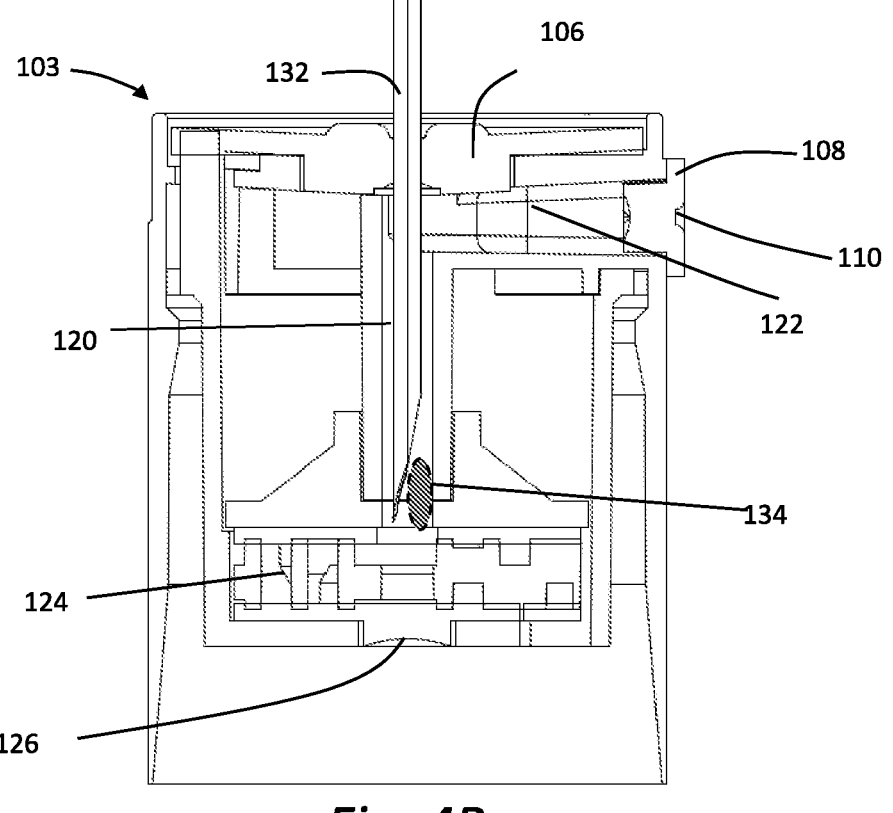
FIG. 4B illustrates a path of insertion of blood into the blood collection tube of FIG. 1B, according to embodiments of the present disclosure.
Figure 5A:
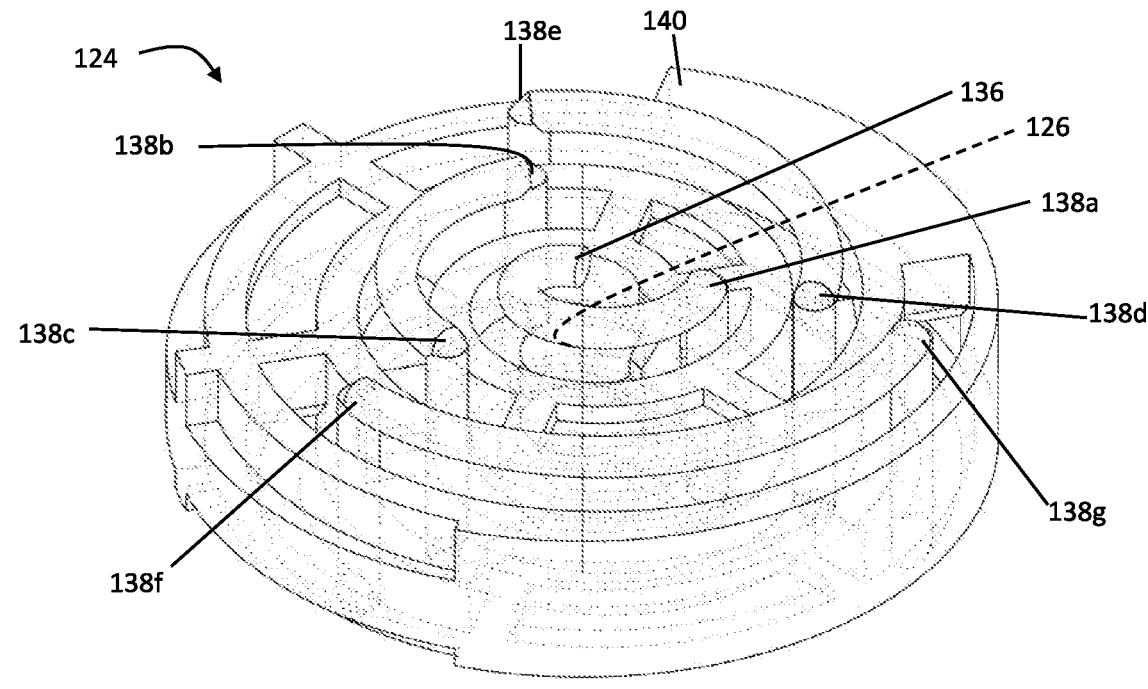
FIG. 5A is an isometric view of a passive mixing labyrinth, according to embodiments of the present disclosure.
Figure 5B:
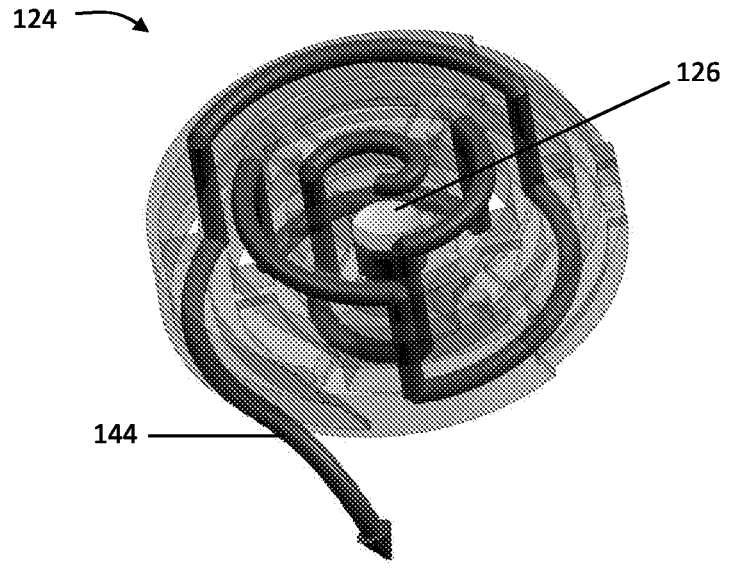
FIG. 5B is an illustration of a path of blood and additive mixing as they pass through the passive mixing labyrinth of FIG. 5A, according to embodiments of the present disclosure.

Cap 103 further includes first conduit 120 and second conduit 122, whose functions are illustrated in FIGS. 4A and 4B, and passive mixing labyrinth 124 and rupture disk 126, whose functions are illustrated in FIGS. 5A and 5B.

Referring to FIG. 4A, first conduit 120 begins at a center of septum 106, and extends axially from septum 106 toward the chamber 112. Second conduit 122 begins at septum 108, and extends radially from septum 108 until meeting first conduit 120. After injection of a blood additive 130 into septum 108 via needle 128, additive 130 passes radially through conduit 122. The additive 130 then passes axially down conduit 120, until arriving at passive mixing labyrinth 124.

Referring to FIG. 4B, blood 134 is injected through septum 106 and into first conduit 120 via needle 132. After exiting the first conduit 120, blood 134 also reaches passive mixing labyrinth 124.

Referring to FIGS. 5A and 5B, passive mixing labyrinth 124 includes a pathway 120 beginning at entrance 136, which is accessed from first conduit 120. The blood 134 and additive 130 pass through numerous turns, including turns 138a-138g shown in FIG. 5A, as well as additional turns on the underside of labyrinth 124. The turns may include both axial turns, such as turn 138a, which cause the blood 134 and additive 130 to turn toward an axial direction of the tube 100, and lateral turns, such as turn 138b, which cause the blood 134 and additive 130 to turn toward a lateral direction of tube 100. The passage of the blood 134 and additive 130 through the turns induces mixing, in a manner known to those of skill in the art. At the end of the pathway, the mixed blood and additive 144 exit the labyrinth at exit 140. Exit 140 is located at a radial periphery of the labyrinth 124.

The layout of labyrinth 124 depicted in FIGS. 5A and 5B is merely exemplary, and other configurations and pathways may also be used, so long as they effectively mix the blood and additive.

In preferred embodiments, the passive mixing labyrinth 124 causes the blood and additive to mix at least ten times as they travel together along the pathway. The labyrinth 124 depicted in FIGS. 5A and 5B meets this objective. This is advantageous because, in prior art blood collection systems, the phlebotomist inverts the blood collection tube 1 manually up to ten times in order to mix the blood and the additive. Labyrinth 124 thus replaces this manual mixing with a passive mixing process, achieving optimum results.

Rupture disk 126 is inserted or over-molded at the center of passive mixing labyrinth 124. The purpose of rupture disk 126 is twofold. During the collection of the additive 130 and blood 134, the rupture disk 126 serves as the end of first conduit 120. The rupture disk thus prevents travel of the blood 134 and additive 130 beyond opening 136. In addition, during sampling of the mixture 144 from the chamber, a probe may be inserted into the chamber through rupture disk 126, as will be illustrated in connection with FIGS. 7A-7C.

Figures 6A, 6B:
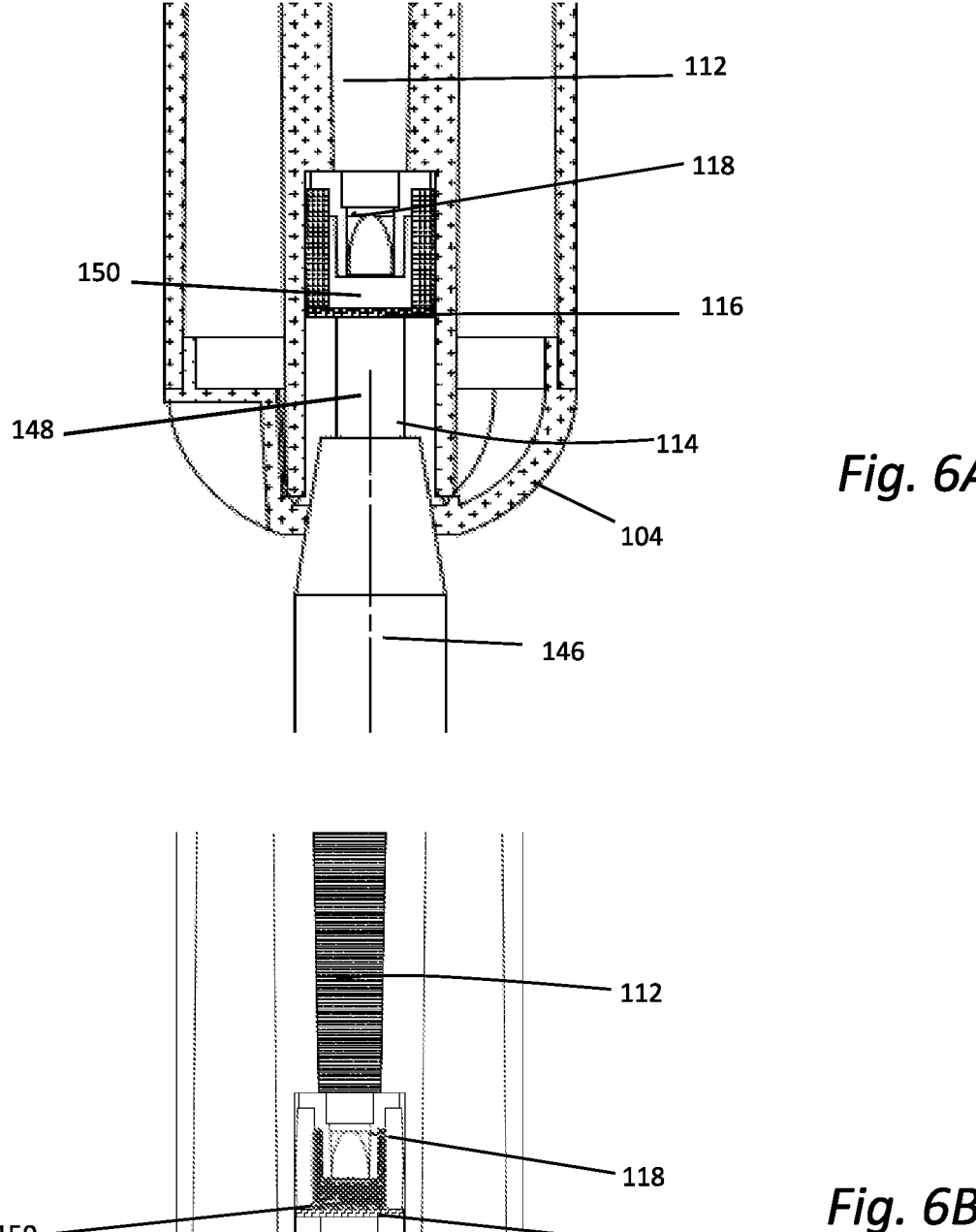
FIG. 6A is a cross-section view of a vacuum pump tube applied to a vacuum port of the blood collection tube of FIG. 1B, according to embodiments of the present disclosure.
FIG. 6B illustrates the operation of a valve and a moisture non-permeable membrane at the vacuum port, for sequestering blood from the vacuum port, according to embodiments of the present disclosure.

FIGS. 6A and 6B illustrate the insertion of a vacuum tube 146 into an interior region 148 of vacuum port 114, and various components of the distal end of tube 100. Membrane 116 is configured between vacuum port 114 and chamber 112. Membrane 116 is configured to permit vacuum to be drawn therethrough but is non-permeable to liquid. For example, the membrane 116 may be made of a polytetrafluroethylene (PTFE) or of a thin silicone membrane. One-way valve 118 is configured between a distal end of chamber 112 and membrane 116. Valve 118 is made of a material that is approved by regulatory agencies for contacting blood samples, such as silicone. Valve 118 is controlled by the force of a vacuum applied at port 114. Region 150 is defined between the valve 118 and the membrane 116. When a vacuum is applied to vacuum port 114, blood is drawn through valve 118, and fills region 150, as shown in FIG. 6B. This blood is sequestered from the distal end of the chamber by the valve. Advantageously, the sequestering of the blood in region 150 from the rest of the blood in the chamber prevents any contamination of the blood by the membrane 116, which could affect the accuracy of an assay of the blood.

Figures 7A, 7B, 7C:
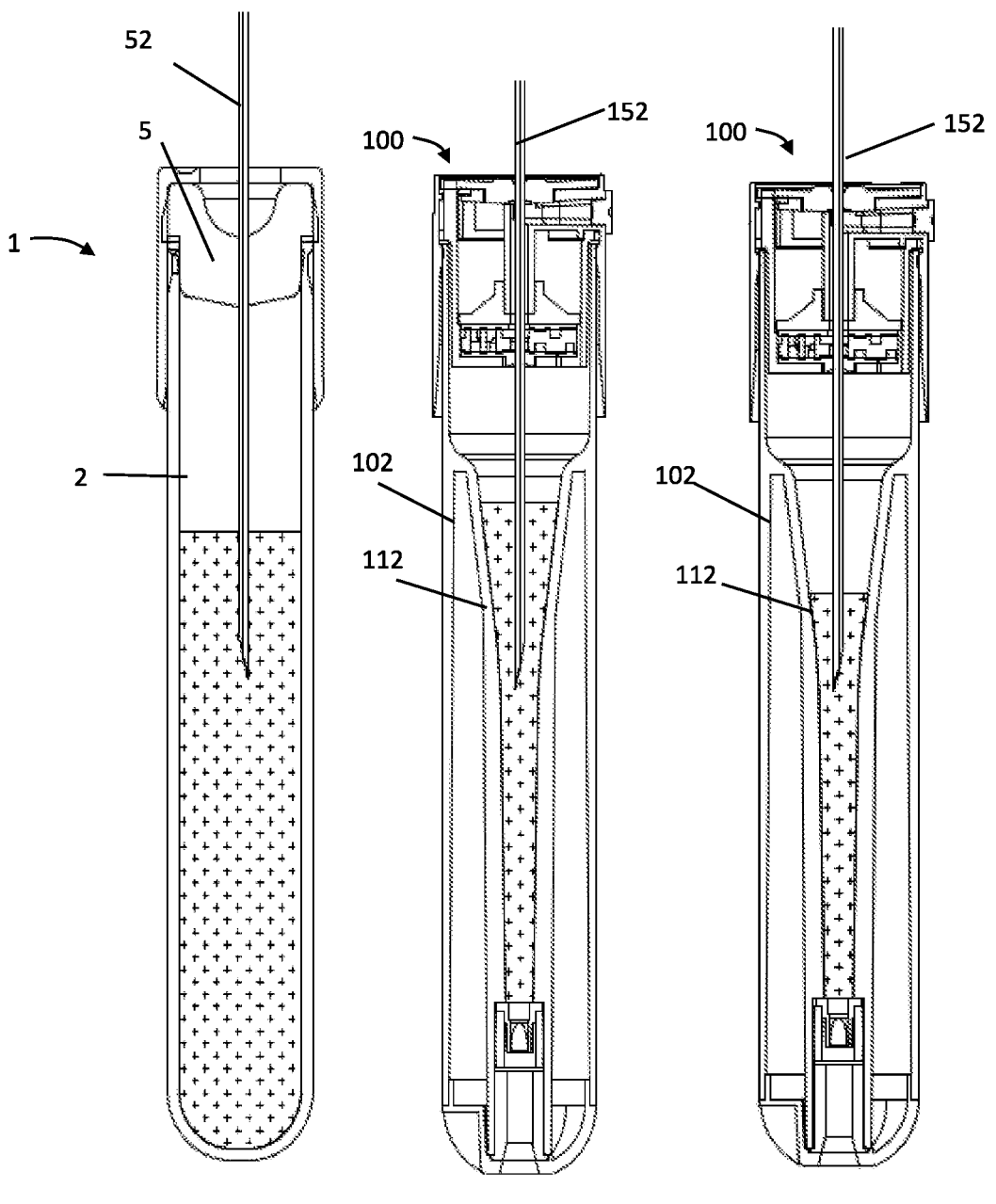
FIG. 7A illustrates the prior art blood collection tube of FIG. 1A filled with blood.
FIG. 7B illustrates the blood collection tube of FIG. 1B filled with 1 ml of blood, according to embodiments of the present disclosure.
FIG. 7C illustrates the blood collection tube of FIG. 1B filled with 300 μl of blood, according to embodiments of the present disclosure.

FIGS. 7A-7C illustrate how tube 100 is fully compatible with existing laboratory equipment for sampling blood collected in a blood collection tube. Referring to FIG. 7A, prior art tube 1 is shown filled with blood at a typical height. Probe 52 is inserted into septum 5 at a typical height, from which blood may be withdrawn. Referring now to FIG. 7B, tube 100 is shown filled with 1 ml of blood. Because of the shape of chamber 112, the blood fills the chamber 112. Thus, probe 152, which is identical to probe 52, may easily be inserted through septum 106, puncture the rupture disk 126 (described above in connection with FIGS. 4B and 5B), and access the blood within chamber 112. In FIG. 7C, only 300 μl of blood is collected in chamber 112. Chamber 112 is shaped such that the cylindrical-shaped lower section holds less than the collected 300 μl, and accordingly at least a portion of the collected blood is in the cone-shaped upper section of chamber 112. As a result, probe 152 is easily able to collect blood from the upper section of chamber 112, without having to be longer or thinner than probe 52.

Figures 8A, 8B:
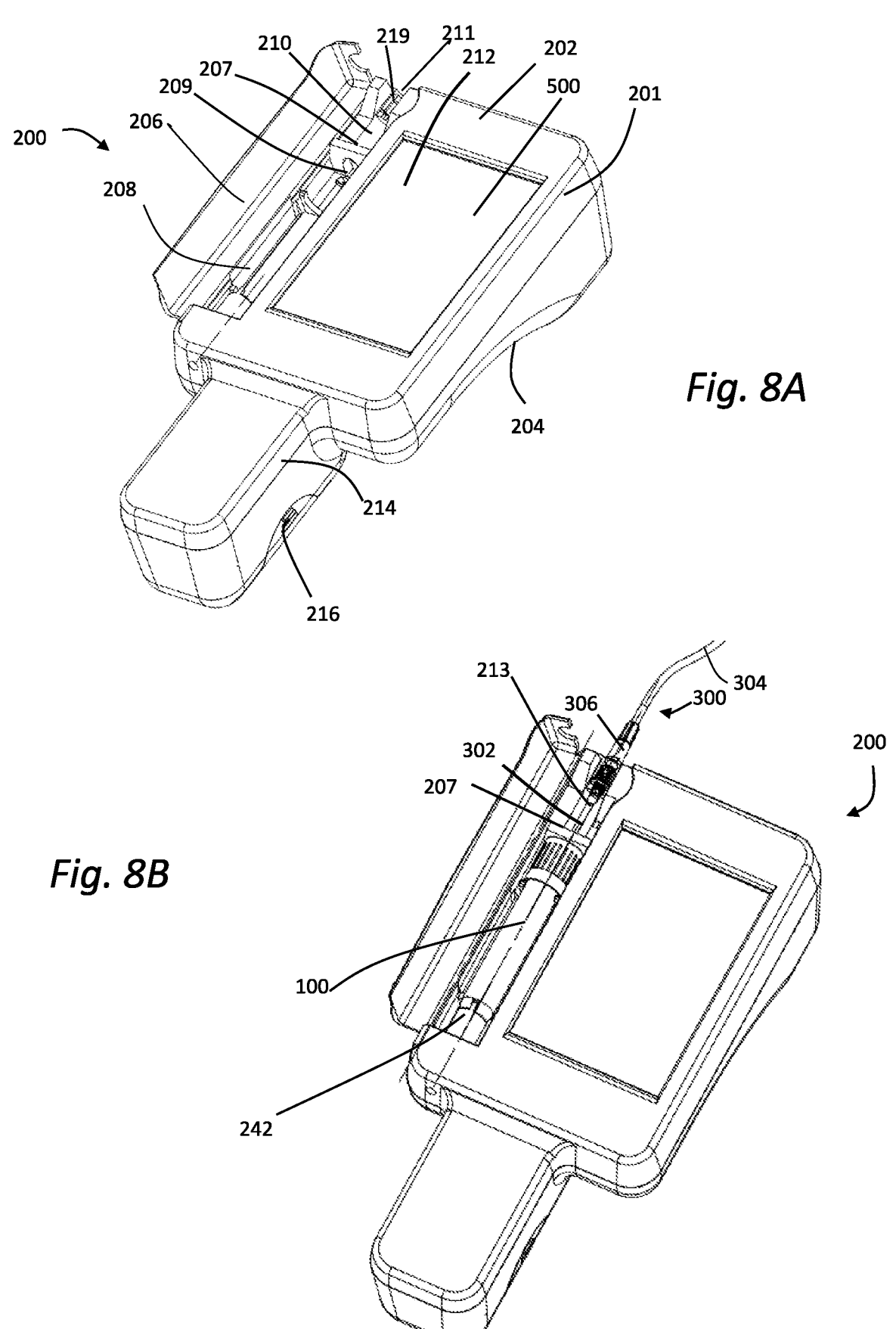
FIG. 8A is an upper perspective view of a blood collection device, according to embodiments of the present disclosure.
FIG. 8B is an upper perspective view of the blood collection device of FIG. 8A with a blood collection tube and a blood needle contained therein, according to embodiments of the present disclosure.

Referring now to FIGS. 8A-12C, blood collection device 200 is configured to withdraw blood and additives into blood collection tube 100. FIG. 8A depicts an upper perspective view of device 200 without a tube therein, and FIG. 88 depicts the same view of device 200, with a tube 100 therein. FIG. 8C depicts a lower perspective view of device 200.

Device 200 includes casing 201, and has an upper face 202 and a lower face 204. Casing 201 is ergonomically shaped for multiple grip positions, for both right-handed and left-handed users.

Cover 206 is attached to the casing 201, for example via a hinged connection. Cover 206 covers first slot 208 and second slot 210. Cover 206 may be opened to permit insertion or removal of tube 100, and is closed and optionally locked during operation of device 200.

First slot 208 is configured for receiving therein tube 200, and second slot 210 is arranged for receiving therein a needle 304. Needle 304 is part of a phlebotomy assembly 300 including a venipuncture cannula (not shown), tubing 302 extending from the venipuncture cannula, needle 304, and connector 306 for connecting the needle 304 with tubing 302. A divider 207 is configured between first slot 208 and second slot 210. The divider 207 has a central aperture 209 for permitting needle 304 to pass therethrough. Similarly, cover 206 has an aperture 211 parallel to aperture 209, for permitting the needle 304 to pass therethrough, even when the cover 206 is closed. An optical sensor (not shown) may be arranged at divider 207 or central aperture 209. The optical sensor may be used to confirm whether blood has entered the needle 304, for example during a priming process of the tubing 302 and needle 304.

Second slot 210 further includes a locking slot 219. Locking slot 219 is shaped to receive connector 306 and needle 304, and is slidable within the second slot 210. The second slot 210 may also have a locking tube 213 for receiving the needle 304 therein. When the needle 304 is received in locking slot 219 and locking tube 213, and the needle 304 is advanced relative to the second slot 210, the locking slot 219 and locking tube 213 advance with it. The advancing locking tube 213 pushes tube 100 within first slot 208. Tube 100 is pushed sufficiently forward by the locking tube 213 so as to be flush with vacuum adapter 242. In alternative embodiments without a locking tube 213, a similar pushing function may be performed by the needle 304 or connector 306 itself. The locking slot 219 may be locked into place with a spring-loaded mechanism that is attached to a sensor (not shown).

Optionally, locking slot 219 and needle 304 may be advanced, locked, and retracted in an automated fashion, between three positions: a rest position, in which the tube 100 is not flush with vacuum adapter 242; a vacuum position, in which the tube 100 is flush with vacuum adapter 242 but the needle 302 is not piercing septum 106; and a drawing position, in which the needle 302 is advanced so that it is piercing septum 106. The locking slot 219 may be controlled by any suitable motor, such as a servo motor. The needle 304, locking slot 219, and tube 100 stay in place until completion of a blood collection process, at which point the locking slot 219 is automatically released, causing automatic retraction of locking slot 219 and ejection of the needle 304 from tube 100. The view of FIG. 8B shows the tube 100, locking slot 219, and locking tube 213 in this released position. The foregoing descriptions of locking slot 219 and locking tube 213 are merely exemplary, and any other suitable mechanism may be employed for releasably locking the needle 304 and tube 100 in place.

Screen 212 is also visible within upper face 202. Screen 212 may be a touch screen. The touch screen 212 may be any standard screen or display suitable for implementation in a mobile computing device, such as LCD, OLED, AMOLED, Super AMOLED, TFT, or IPS. The screen displays a graphic user interface 500 for operation of device 200, which will be described in further detail in connection with FIGS. 14A-14F.

Screen 212 is integrated with a processor (not shown) for controlling of operations of device 200. The processor includes a memory, and circuitry for executing computer readable program instructions stored on the memory. The memory is a non-transitory storage medium having stored thereon code instructions that, when executed by the processor, causes performance of various steps. The storage medium may be, for example, an electronic storage device, a magnetic storage device, an optical storage device, a semiconductor storage device, or any suitable combination of the foregoing. In particular, the functions described herein may be programmed a computer program product installed on the non-transitory computer readable medium of the processor. In exemplary embodiments, the screen 212 functions as an input interface for the processor, including for confirming predetermined volumes of blood additive and blood to be delivered into tube 100.

In addition, the processor preferably includes wireless communication hardware, such as Wi-Fi or Bluetooth, for transmitting information between the device 200 and an external device, such as a facility computer system, a smart phone, or a tablet. Alternatively or in addition, device 200 includes a manual data port, such as a USB connection, for interfacing between the processor and the external device. Through the link to the facility system, the processor is used to control patient information, sample collection compliance, specimen quality optimization, documentation compliance, and to provide a complete inventory and storage management. The data link may also be used to provide programming, maintenance, and software updates to device 200. A computer program product for controlling and documenting patient blood draws may be installed on both the facility computer system and on device 200, for ease of compatibility and information transfer.

Optionally, the screen 212 and processor are part of a tablet computer that is installable within, and removable from, device 200. Alternatively, the screen 212 and processor may be permanently fixed within device 200.

The processor is connected to various sensors in device 200, including a sensor for determining whether cover 206 is open or closed, a sensor for determining whether locking tube 213 is in a locked or unlocked position, and other sensors that will be described further herein.

Figures 9, 10:
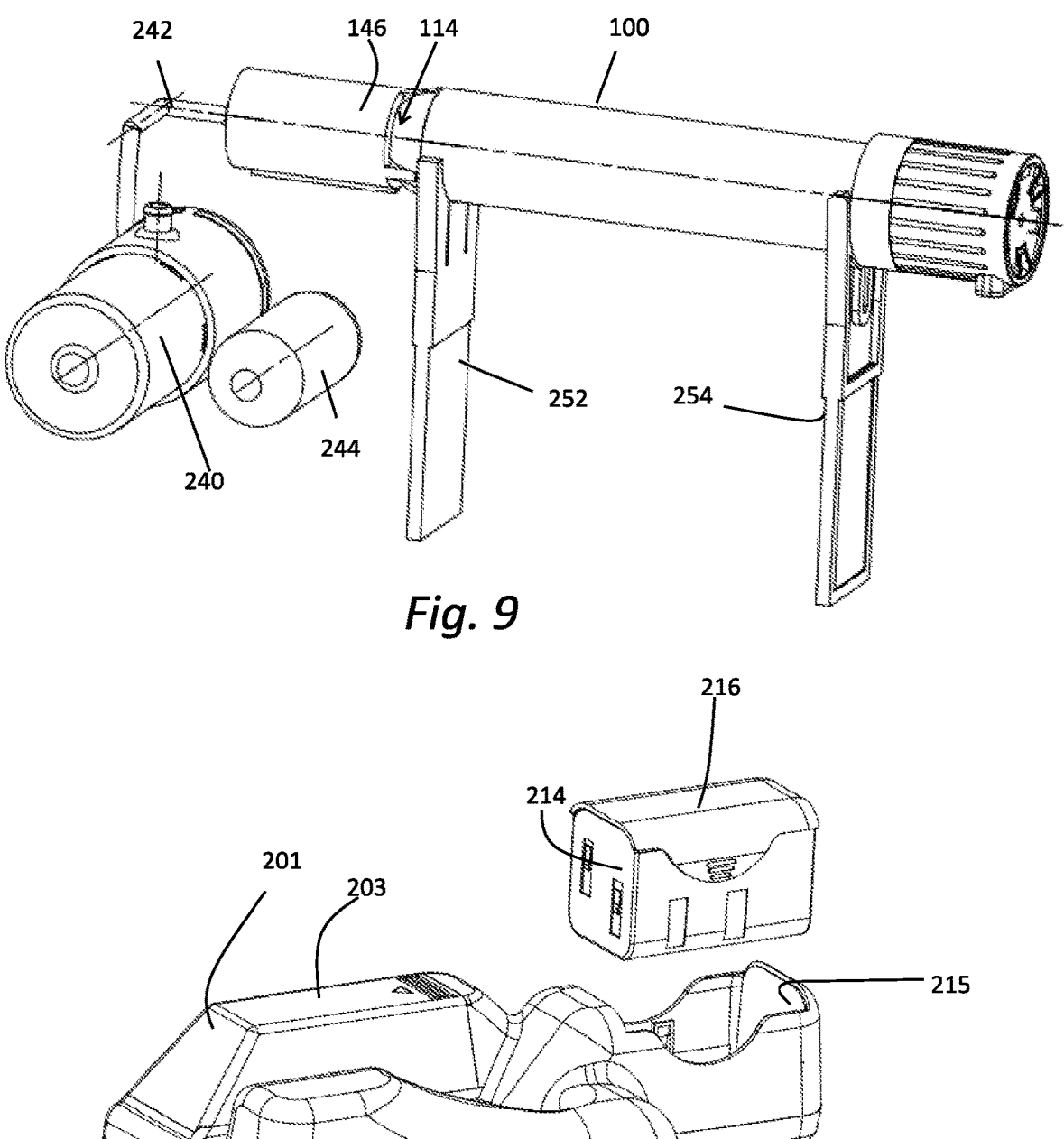
FIG. 9 is a perspective view of vacuum pump of the blood collection device of FIG. 8A connecting with a vacuum port on the blood collection tube of FIG. 1B, according to embodiments of the present disclosure.
FIG. 10 is a perspective view of a battery and a corresponding battery slot of the blood collection device of FIG. 8A, according to embodiments of the present disclosure.

Device 200 further includes battery 214, which is stored within battery case 215 (shown in FIG. 10). Battery case cover 216 secures battery 214 within battery case 215. Battery 214 may be any battery known to those of skill in the art, such as lead-acid, nickel cadmium, nickel-metal hydride, lithium-ion, lithium-ion polymer, or an alkaline battery. In advantageous embodiments, battery 10 is rechargeable. Because device 200 is battery-powered, device 200 is fully portable. Battery 214 is configured to last throughout a typical user's workday.

In addition to being portable, in preferred embodiments, device 200 is handheld. That is, the device 200 is capable of being held by a technician during use thereof. In further advantageous embodiments, the device 200 may be held within a single hand, so that a technician may use one hand to hold the device 200, and another hand to insert or remove a needle or collection tube. In preferred embodiments, the size of device 200 is comparable to that of handheld printers currently known to those of skill in the art, for example, Zebra® printers.

Figure 8D:
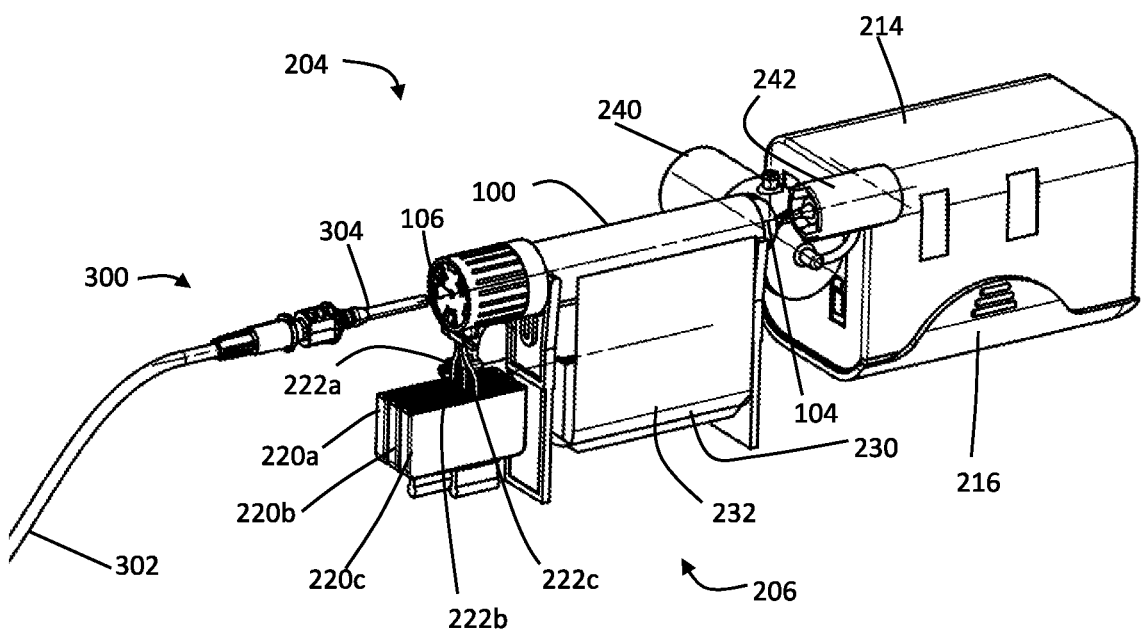
FIG. 8D is an upper perspective view of the blood collection device of FIG. 8A with its casing and certain internal components removed, according to embodiments of the present disclosure.
Figure 8E:
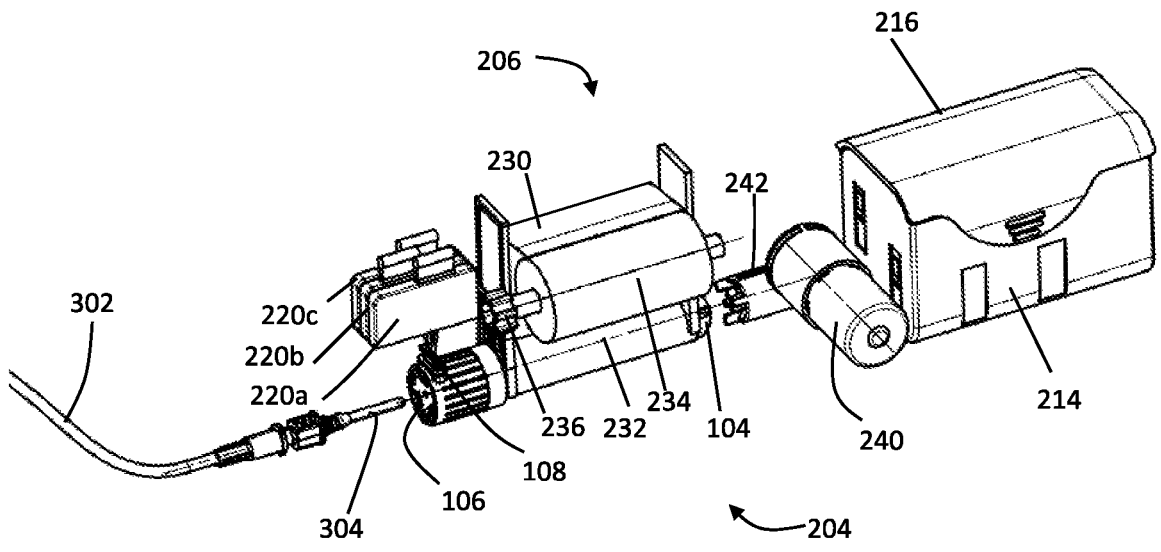
FIG. 8E is a lower perspective view of the blood collection device of FIG. 8A with its cover and certain internal components removed, according to embodiments of the present disclosure.

FIGS. 8D and 8E depict device 200 with casing 201 and certain other internal components removed. In the view of FIG. 8D, top side 204 is on the top and bottom side 206 is on the bottom; in the view of FIG. 8E, these orientations are reversed.

Reservoirs 220a, 220b, and 220c store blood additives. Although in most of the examples described below, reservoirs 220 contain liquid additives, the term "reservoir" encompasses a store of a solid additive. Typically, each reservoir 220a-c stores a different additive. For example, the reservoir 220a may store a concentrated solution of sodium heparin or lithium heparin; reservoir 220b may store a concentrated solution of potassium EDTA, and reservoir 220c may store a concentrated solution of sodium citrate. The number of reservoirs, and the type of additive in each reservoir, may be modified without departing from the scope of the present disclosure. A plurality of conduits 222a, 222b, 222c are respectively connected to a corresponding reservoir 220a, 220b, 220c. Each conduit 222 extends from a respective reservoir 220 toward septum 108 of tube 100. The specific mechanism for delivery of a blood additive from a reservoir 220 through conduit 222 will be described further in connection with FIGS. 11A-11B.

Also visible in FIGS. 8D and 8E is printer 230, whose location is indicated schematically. Printer 230 may be, for example, a thermal printer or a color micro printer. A roll of adhesive-backed labels 234 is arranged adjacent to printer 230. A single label 232 is extending upward from the roll 234 toward tube 100. Roller 236 is used to advance roll 234 as the printer 230 is printing. The printing and labeling system is illustrated in greater detail in FIGS. 12A-12C.

Device 200 further includes vacuum pump 240, as shown particularly in FIG. 9. Vacuum pump 240 may be a micro-diaphragm gas sampling pump. Vacuum pump 240 includes adapter 242 for receiving therein the bottom of tube 100, and making a vacuum-tight seal therewith. The interaction between pump 240 and tube 200 is further shown in FIG. 9. The tube 100 rests on stands 252, 254, with the bottom 104 at a rear portion of the device 200. Vacuum tube 146 extends from adapter 242 and is insertable into the vacuum port 114 of the tube 100, in the manner discussed above. The specific vacuum drawn by the vacuum pump through vacuum tube 146 may be controlled by the processor, for example, through the use of sequencing valves.

Optionally, vacuum pump 240 is connected to a vacuum reservoir or staging chamber 244 for storing a vacuum. The stored vacuum may be used to enable a quicker or more controlled application of a vacuum onto a tube 100.

Referring to FIG. 10, device 200 further includes a barcode scanner 205, whose location is schematically indicated within casing 201. Barcode scanner 205 is used to scan a barcode on an armband of a patient, in order to verify the patient's identity. Other sensors may alternatively be used to confirm patient identity, including, for example, image sensors. Device 200 also includes a removable cover 203 for inserting and removing reservoirs 220a-220c as well as for inserting and removing ink cartridges for printer 230.

Figure 11A:
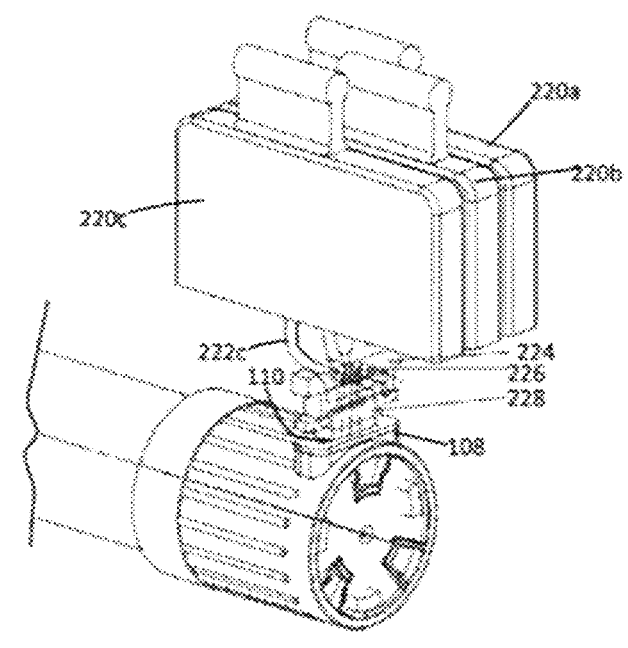
FIG. 11A is a lower perspective view of a system for delivering blood additives from plurality of liquid reservoirs to a septum of the blood collection tube of FIG. 1B, according to embodiments of the present disclosure.
Figure 11B:
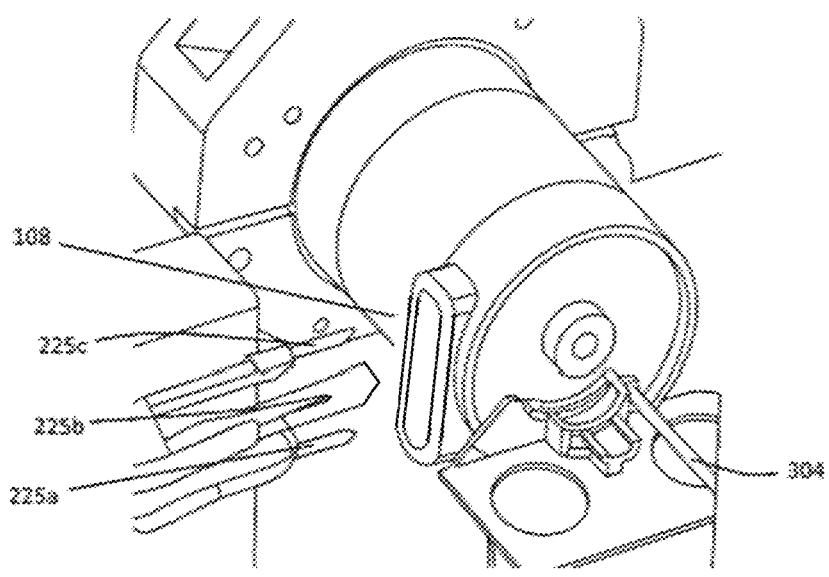
FIG. 11B is an illustration of a needle from a blood additive reservoir injecting a blood additive into a blood collection tube, according to embodiments of the present disclosure.

FIGS. 11A-11B illustrate in greater detail the system for delivering blood additives from the reservoirs 220a-220c, through conduits 222a-222c, and into septum 108 of tube 100, according to embodiments of the present disclosure. As shown in FIG. 11A, valve assembly 224 is configured between each respective reservoir and an outlet of each conduit 222a, 222b, 222c. Valve assembly 224 contains, for example, a plurality of solenoid valves, each configured to control flow of fluid through a respective conduit 222. The system further includes an air intake 226 and a sensor 228 configured to monitor flow of fluid through each valve in valve assembly 224. Sensor 228 may be, for example, any type of flow meter known to those of skill in the art. As shown in FIG. 11B, each conduit 222a-222c terminates in a needle 225a-225c. Each needle 225a-225c is operatively connected a motor, such as a servo motor having a position encoder, configured to extend and retract the needle.

A process of drawing a blood additive from a reservoir 220 into a tube 100 using vacuum pump 240 is as follows. First, an identity and volume of blood additive to be drawn is set with the processor. Upon determination of a volume of fluid to be delivered from a particular reservoir 220, the processor directs operation of the servo motor so that the needle 225 corresponding to that reservoir 220 extends and penetrates the septum 108, as shown in FIG. 11B. The processor further directs opening of a valve within valve assembly 224 corresponding to the selected additive. The opening of the valve permits additive to be drawn out the selected reservoir 220. A vacuum is applied by vacuum pump 240, drawing a vacuum through tube 100, including through first conduit 120 and second conduit 122, through needle 225, and through conduit 222. As a result, the additive is drawn from reservoir 220. When sensor 228 determines that the predetermined volume of additive has passed through the valve 224, the processor directs closure of the valve, and opens air intake 226. Air intake 226 delivers a small pocket of air behind the aliquot of concentrated blood additive, to help drive the aliquot through the conduits 222, needles 225, and first and second conduits 120, 122 of the tube. The vacuum is then turned off, and the needle 225 is removed from septum 108.

Alternative methods for delivery of additives from reservoir 220 include piezo or inkjet delivery.

In the above-described embodiments, the blood additives are provided as highly concentrated liquid solutions. The concentration is determined such that a quantity of up to around a 10 µl aliquot of the solution is sufficient for providing additive to a blood draw of up to 1 ml. For example, lithium heparin may be delivered either at 15.8 USP (United States Pharmacopeia units) per unit or pulled as a 10 µl aliquot from a solution that has equivalent 1580 USP. EDTA may be provided in a super concentrate that contains 180 mg of EDTA for every 10 µl aliquot. These concentrations are merely exemplary, and other concentrations may also be employed.

One advantage of the use of concentrated liquid solutions is that the blood additives are removed from needles 225 without requiring any liquid or outside material to contact the tips of needles 225. As a result, it is possible to use the same delivery system to deliver blood additives to multiple tubes 100, without any risk of contamination. In addition, because there are separate conduits 222 for each blood additive, and separate regions 110 on septum 108 for receiving the different additives therethrough, there is no possibility of contamination of any particular reservoir 220 or conduit 222 with a blood additive from a different reservoir or conduit.

In alternative embodiments, the blood additives may be delivered as solids. For example, the blood additives may be delivered with a screw conveyor system, wherein the tip of each screw conveyor is configured as a needle that is insertable into septum 110. The device may also use a combination of liquid and solid delivery as needed, with the liquid and solid additives being delivered from separate reservoirs 220.

In addition, in alternative embodiments, instead of using vacuum pump 240 for withdrawing the blood additives, a separate delivery system is implemented for the blood additives. For example, the separate delivery system may include a vacuum push-pull system configured at the reservoirs 220.

FIGS. 12A-12C illustrate a process of printing an adhesive-backed label and attaching the label onto a tube, according to embodiments of the present disclosure. During or following collection of blood into a tube 100, printer 230 prints a label 238. Label 238 may have information such as the patient name, the time of the sampling, and the type of additive. Such information may be encoded in a bar code. The printing may be at least partially in color, in order to provide color coding, similar to the color coding of caps 3 in prior art evacuated blood collection tubes 1. As shown in FIG. 12A, following printing of a label 238, the roller 236 rolls the label 238 in a generally upward direction. Thus, the printed label 238 is aligned with body 102, while blood collection tube 100 is still in the first slot. The adhesive then attaches to the body 102, as shown in FIG. 12B. As roller 236 continues to roll, label 238 and the body 102 roll correspondingly, in the direction of the arrow. Thus, roller 236 is also configured to rotate body 102 within first slot 208. This rolling causes the printed label 238 to be applied in its entirety to the exterior of blood collection tube 100.

While device 200 is depicted in the illustrated embodiments as a standalone device, it is also possible to integrate device 200 in a larger device. For example, a robotic surgery device, whether for general surgery or for orthopedic surgery, may include a blood sampling module having all of the operative components of device 200.

Referring now to FIG. 13, a method 400 of drawing blood into tube 100 with device 200 is disclosed.

At step 401, a user scans a bar code associated with a patient. The bar code may be printed on an armband worn by the patient. The processor determines patient information based on the scanned bar code, for example, the patient's name and current location. The processor compares the patient information to stored patient information which had been previously downloaded to the device 200. For example, the processor may have stored thereon a list of patients and bar code information for which blood drawing is required. The processor may allow proceeding to a next step of blood collection only when the patient's name and scanned bar code information matches one of the names and bar codes on the list. This prevents error due to misidentification.

At step 402, the device 200 displays information regarding how much blood to collect from the patient, which blood additives to include in each tube, in which order, and any special instructions associated with that patient, such as drawing at especially low vacuum. The volumes of blood and additives to be collected are predetermined. For example, a physician may order a list of assays, and the laboratory information system, or the processor of device 200, sets the volume of blood required to be collected in order to perform such assays. The processor or computer program may further calculate a predetermined volume of blood additive that is necessary to add to each such sample of blood in order to preserve the blood for testing.

At step 403, the technician inserts a blood collection tube into first slot 208 and closes cover 206. Because the blood collection tubes 100 are all interchangeable, this step may be performed prior to any of the preceding steps. Blood collection tube 100 is maintained at atmospheric pressure prior to insertion into first slot 208. As used in the present disclosure, "atmospheric pressure" refers to ambient pressure of an environment in which the blood drawing process is performed.

Optionally, if the door is not closed and locked into place, an error message appears, and the screen does not proceed to the remaining steps.

At step 404, the user inserts an intravenous cannula into a vein. The user may perform this step manually, in the manner known to those of skill in the art. For example, the technician may insert a winged needle set into the vein. The cannulation and drawing of blood may alternatively be performed by a phlebotomy robot.

At step 405, the technician inserts the needle 304 into the second slot 211. The technician locks needle 304 into place using locking slot 213 and/or locking tube 219.

At step 406, the user primes the system. The priming may occur automatically or in response to user instruction. The optical sensor determines that the system is primed, by sensing the presence of blood in the tubing 302 or needle 304.

At step 407, device 200 draws a volume of blood additive solution from the appropriate reservoir and into blood collection tube 100, by applying vacuum at the vacuum port 114. This step may be performed in the manner described above in connection with FIGS. 11A-11B. Specifically, a vacuum is applied to the blood collection tube 100 while the cap 103 of the blood collection tube 100 is fluidically connected to a reservoir 220 containing the blood additive.

The volume of blood additive is added to the tube according to a predetermined ratio of additive to blood. The ratio may be, for example, about 1:100. Thus, for a 500 μl sample of blood, 5 μl of additive is added. As will be seen further herein, it is possible to deviate up to at least 20% from the predetermined ratio without compromising the accuracy of the blood tests.

The vacuum is applied for a particular period of time. Specifically, the vacuum is applied for a sufficient amount of time to withdraw the blood additive into the second conduit 122 and first conduit 120, but not to withdraw the blood additive further into blood collection tube 100. Because a very small volume of blood additive is drawn, it is possible to fit the entire volume of drawn blood additive in the second conduit 122 or first conduit 120. Optionally, the drawn blood additive collects at the bottom of the first conduit 120, at rupture disk 126.

At step 408, device 200 draws a volume of blood from needle 304 into blood collection tube 100. This drawing step is thus performed by applying a vacuum to the blood collection tube, at vacuum port 114, while a cap 103 of the blood collection tube is fluidically connected to an intravenous cannula. One advantage of inserting the blood only after insertion of the additives is that there is no potential for contaminating the remaining additives in the reservoirs 220 and conduits 222 with blood.

In exemplary embodiments, the applied vacuum may be approximately 120-150 mm Hg. The specific applied vacuum may be selected based on various factors, such as the desired time required for collection of the blood. The volume of withdrawn blood may be, for example, between 300 and 1,000 μl, or more pending usage. The vacuum is applied until the predetermined volume of blood is collected, at which point the vacuum ceases automatically.

Typically, steps 407 and 408 are performed in very close proximity, i.e., within a few seconds of each other. Theoretically, it is possible for steps 407 and 408 to happen simultaneously, so long as the needle delivering the additive is not contaminated by blood. This may be ensured through various mechanisms, including controlling the depth of insertion of the needle containing the additive and the needle containing the blood.

The drawing of the additive and blood proceeds automatically, once the user initiates the priming process. Throughout the collection process, a technician may have the ability to execute an emergency stop to abort the collection. The technician may also control the amount of vacuum that is applied if he or she determines that this is necessary. This adjusting of the vacuum is recorded by the processor and associated with the patient's electronic medical record.

At step 409, the device 200 passively mixes the blood and additive together, by continuing to draw vacuum, so as to draw the blood and additive through passive mixing labyrinth 124. The passive mixing step preferably includes mixing the blood and additive within the passive mixing labyrinth 124 at least ten times. Advantageously, this degree of mixing corresponds to a degree of mixing that would be performed manually by a user on a prior art tube.

At step 410, device 200 prints a label 238 for the blood collection tube 100. As discussed, the label includes the patient name and ID; the additive; a color indicator for the additive type, the date, the time, and the technician ID. The device 200 affixes the label 238 to the blood collection tube 100 by automatically rotating the blood collection tube 100. The process of printing and affixing may be substantially the same as that described in connection with FIGS. 12A-12C.

At step 411, the needle 304 is removed from blood collection tube 100. Optionally, this step is performed automatically, through release of a locking mechanism holding the needle and blood collection tube in place, as described above in connection with FIGS. 8A and 8B. The processor uploads information regarding the blood collection to the facility computer system. This information includes date and time of collection, and identity of the phlebotomist who collected the sample. A button then appears on the graphic user interface instructing the technician to remove the tube 100.

Each of the steps 408-411 are controlled by device 200 with forced compliance, and are documented with traceability.

At step 412, optionally, if the patient requires more than one type of blood assay, a new blood tube is inserted, and steps 407-411 are repeated. The graphic user interface may prompt the user to load the next tube. Upon sensing of locking of the needle into the locking slot again, the processor may prompt the user to select or confirm values for the predetermined volumes of fluid and blood. In the alternative, the volumes of blood and additive may be set for multiple blood collection tubes prior to the first collection of blood and additive. The process is continued until all required tubes are complete.

When all required tubes are complete, a message may be displayed on the graphic user interface. The message may indicate that collection is complete and instruct the user to remove the needle from the patient and bandage the incision point. Another button may appear prompting the user to "Upload Collection Information." When this button is activated, all details of the successful collection are uploaded to the laboratory information system. The patient list is updated with either "complete" (if all tubes are collected) or "partial" (if only some of the requested tubes were collected).

Finally, at step 413, a user withdraws a sample from the blood collection tube for analysis. This user is a lab technician rather than a phlebotomist. Optionally, instead of removing the cap 103 of blood collection tube 100, the user may insert a probe 152 into the cap 103. The probe 152 passes through septum 108, first conduit, 120, and rupture disk 126, to reach the collected blood for sampling, as described above in connection with FIGS. 7B-7C.

FIGS. 14A-F depict graphic user interfaces that may be displayed on the screen 212 during relevant parts of performance of the method 400. The disclosed graphic user interfaces are merely exemplary, and the method may be performed using other interfaces as well.

Method 400 may be performed while device 200 is fully integrated with a hospital information system. The hospital information system includes an electronic medical record (EMR) for each patient. A widely used EMR system in the United States today is the Epic® system, produced by Epic Systems Corporation. The hospital information system interfaces with multiple sub-systems, including a laboratory information system. Each laboratory diagnostic device includes a laboratory instrumentation interface that is operatively integrated with the laboratory information system.

Figures 14A, 14B:
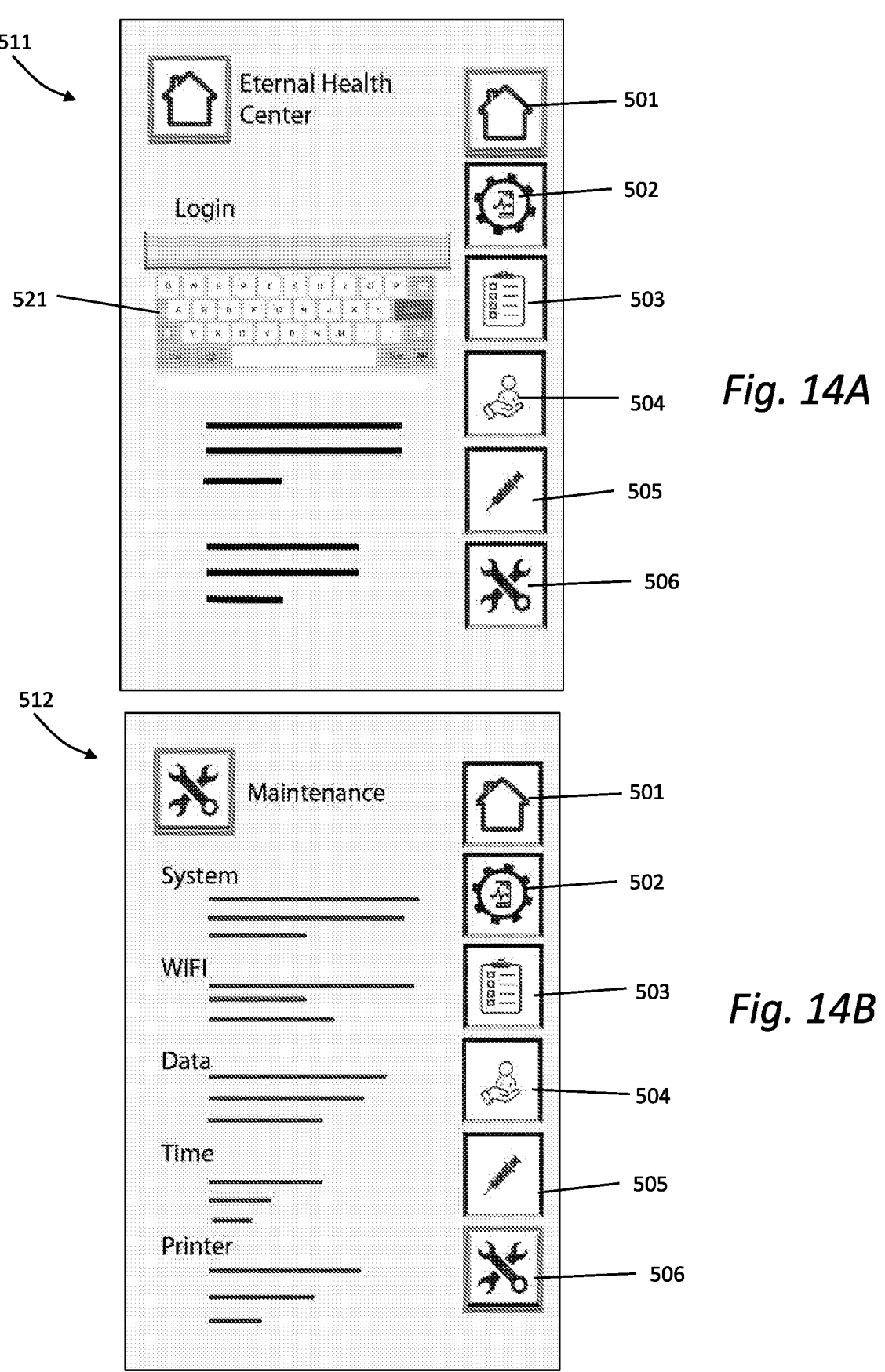
FIGS. 14A-F depict exemplary graphic user interfaces for a display screen of the blood collection device during collection of blood, according to embodiments of the present disclosure.

Referring first to FIG. 14A, when the user turns on device 200, a welcome screen 511 is displayed. A plurality of buttons 501-506 may appear on the margin of the screen 511. The buttons 501-506 represent six different user interfaces for operation of various features of device 200. Button 501 is a "home" button to return the device 200 to the welcome screen 511. Welcome screen 511 includes a login screen with the name of the medical facility. Welcome screen 511 also includes a login field with a keyboard 521, for entering the identity of the user. After a successful login, the login field shows the user ID of the user; if login was unsuccessful, the login field shows an error message. Welcome screen 511 also shows a current date and time.

Button 502 is a status button that may be used to interface with, and obtain information from, the laboratory information system or hospital information system.

Button 506 is a "maintenance" button that takes the user to a maintenance screen 512, shown in FIG. 14B. The maintenance screen 512 includes information relating to matters such as the system, and in particular verifies that the device 200 is connected to the hospital's laboratory information system. Screen 512 may also confirm that a Wi-Fi connection is established between device 200 and the hospital network., Screen 512 may also include information regarding the quantity of on-board consumable supplies such as blood additives, print labels, and ink toner; the amount of battery power left prior to recharging; a number of tubes required in order to complete a series of tasks; and a number of venipuncture steps required to complete a day's tasks. A venipuncture setup may include, for example, alcohol prep wipes, two gauze pads, a tourniquet, a wing needle set, and a bandage.

Figures 14C, 14D:
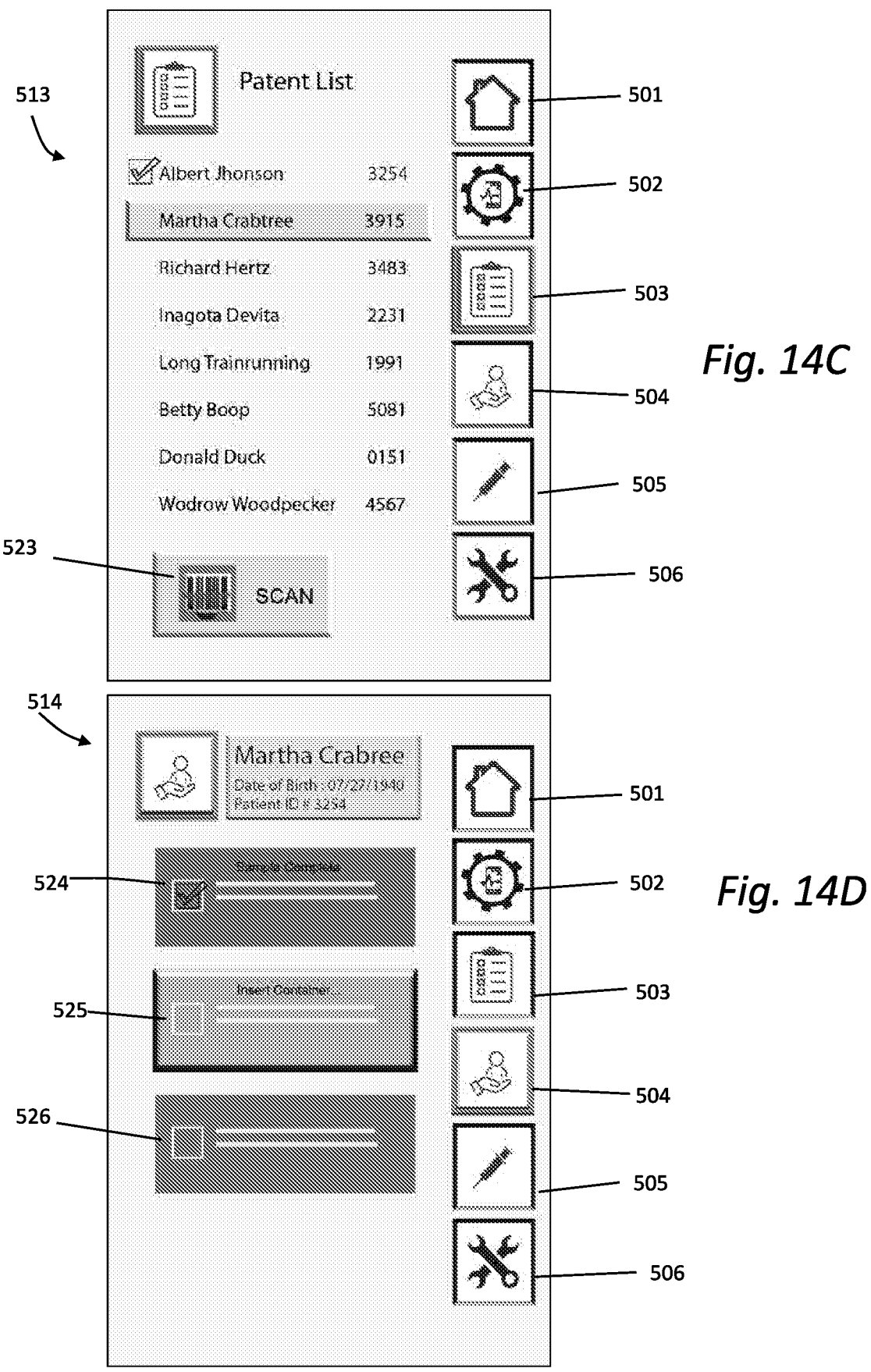

Button 503 is a "patient list" button that calls up patient list interface 513 in FIG. 14C. Interface 513 shows the user a list of patients from which he or she is expected to collect blood, along with the patient's room and bed number. When the number of patients is more than can fit on one screen, there may be an indicator such as "page 1 of 3." The list may be sortable based on patient name or room number. The patient list may be updated in real time, using the wireless connection between device 200 and the facility computer system. This permits addressing of urgent ("stat") requests for blood draws. Optionally, urgent draws may always be listed on top. Patient list interface 513 includes a "scan" button 523, that, when pressed by the user, causes barcode scanner 205 to begin scanning for a barcode. The patient list interface 513 may also include a "close list" button that, when executed, causes recording of all collected specimens as "recorded" in the laboratory information system, and leaves any patients whose blood has not yet been collected to be assigned to another list.

Interface 513 further includes a button 523 for scanning a patient armband. Following a successful scan of a patient's armband, the interface may display an indicator that a positive patient identification is confirmed, and proceed to the next step. Button 523 may be used during performance of step 401. Optionally, absent positive identification, the screen locks and cannot proceed to the next step.

Button 504 is a "selected patient information" button that calls up user interface 514 in FIG. 14D. Interface 514 includes a heading block with information about the patient, such as the name, age, ID number and hospital room number. Interface 514 also includes information blocks 524-526 for communicating information about the status of a blood collection from a particular patient. For example, the information blocks 524-526 may specify that the patient has fragile veins, requiring low pressure blood withdrawal. The blocks may also include messages such as "right arm only," "left arm only," and "bleeding precautions." The blocks may also include instructions for the technician to switch from a standard collection mode to a special collection mode, for example with an extremely low vacuum. The blocks 524-526 may also specify a list of ordered blood collections for that patient, and thus may be displayed during performance of step 402. Advantageously, prior to commencement of the phlebotomy, the user knows how many tubes are needed for that patient, and is able to prepare the tubes in an organized manner.

Figure 14E:
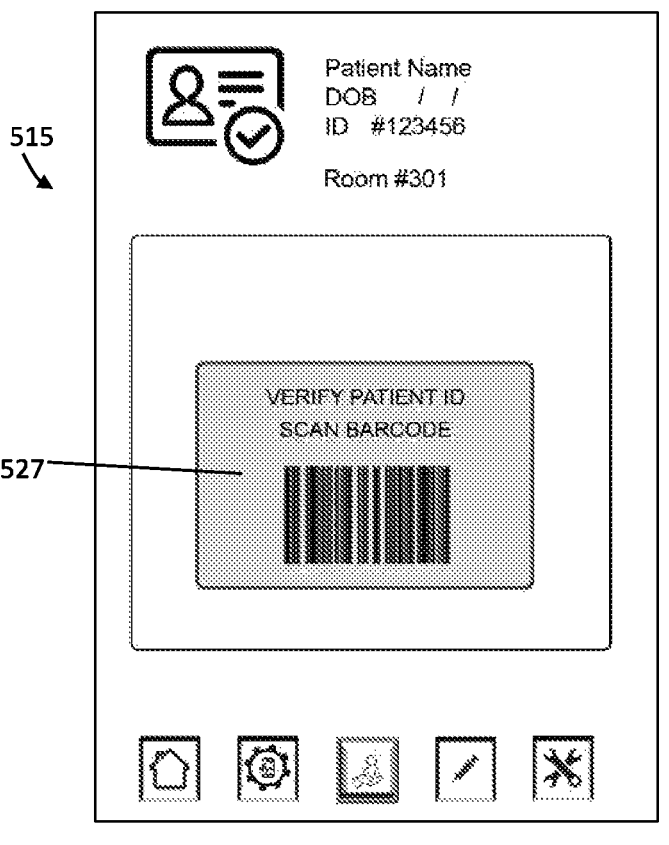

Selection of one of the blocks 524-526 may also lead to user interface 515, shown in FIG. 14E, which includes button 527 for commencing a barcode scan, as described in step 401. The barcode scan has a similar functionality of preventing progression to the next interface until the patient's identity is confirmed.

The graphic user interface of FIG. 14D or FIG. 14E may be displayed during performance of steps 403-405, through insertion of the needle into the second slot. Following detection of the secure insertion of the needle 304 into second slot 211, a "Start Collection" button may appear. Depression of the "Start Collection" button causes the screen to display user interface 516.

Figure 14F:
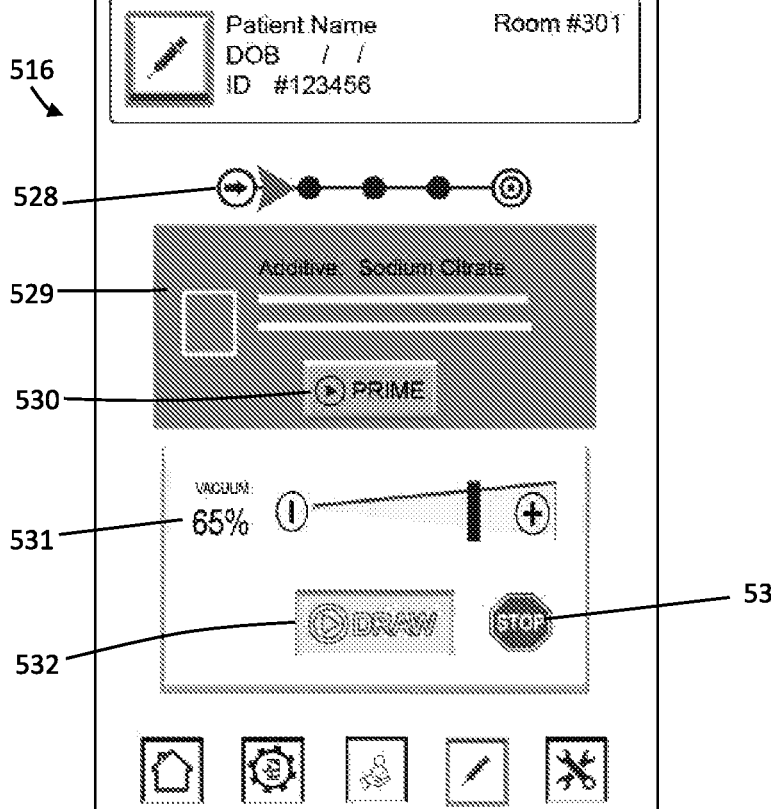

FIG. 14F depicts a "collection control" graphic user interface 516 that is called up on screen 212 prior to and during withdrawal of blood, i.e., during performance of steps 406-412. At the top, a patient name, date of birth, ID number, and room number are listed. User interface 516 includes a status line 528 for displaying a status of the blood collection. Box 529 identifies the additive that is selected. Box 529 may be color coded, according to the color coding system used for classifying prior art blood collection tubes.

Box 530 is a "priming" button that may be used to execute priming step 406. The priming button 530, which instructs device 200 to prime a tube 100 and/or tubing 302 attached to a needle 304, without withdrawing of any fluid or blood into a tube 100. Depression of the priming button 530 commences the priming process. In the alternative, the priming may occur automatically upon detection of a tube 100 and needle 304 secured in their respective locations, as discussed above.

Vacuum control slider 531 displays the designated amount of vacuum that is applied. The slider 531 may be adjusted if the technician determines that this is necessary, as discussed above in connection with step 407. In addition, emergency stop button 533 may be depressed in order to abort the collection, as also discussed above in connection with step 407

FIGS. 15A, 15B, 16A, and 16B depict experimental results for blood assays performed with concentrated liquid blood additives, similar to those that would be delivered using device 200, as compared to a blood assay performed on blood collected using prior art evacuated tubes. Specimens were collected from volunteer donors using both standard Vacutainer® tubes (Becton Dickinson) as controls, and tubes containing the concentrated liquid blood additives used in reservoirs 220. The samples were sent to a national reference lab for analysis of the two most common test panels.

FIG. 15A reports results of a CBC testing panel with EDTA blood additive for a single patient (number 419), and FIG. 15B reports results of a plasma sample with lithium heparin blood additive for the same patient.

Figure 16A:
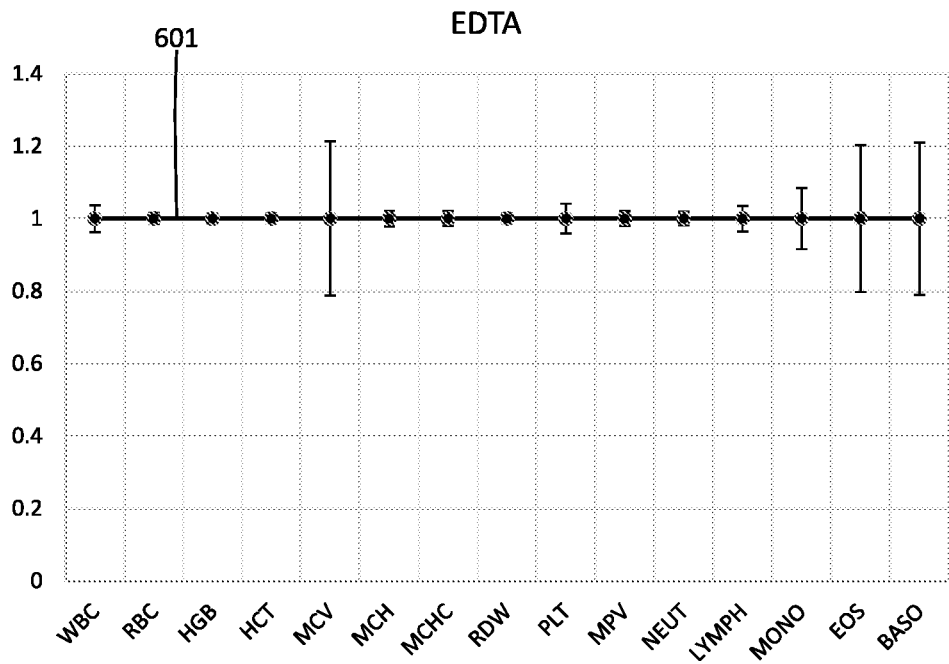
FIGS. 16A-16B illustrate a normalized view of the results shown in FIGS. 15A and 15B, according to embodiments of the present disclosure.

FIGS. 15A and 16A present the values in tabular form, with each row being a given analyte. The four columns are the control, taken with evacuated tubes; and three tests performed with blood collected using the devices and methods described above. In the second column, the blood additives were added to the blood at a ratio of 120% relative to the target ratio; in the third column, the additives were added at the target ratio; and in the fourth column, the additives were added at a ratio of 80% relative to the target blood ratio.

The statistical overlap between the controls and the test data is extremely strong, as quantified by a regression analysis, Anova, and student t-test. Specifically, at the 80% value, the multiple R value was 0.9994, the R-squared value was 0.9988, and the adjusted R-squared value was 0.9986. The standard error was 1.6039. For the 100% test, which was the best-performing, the R value was 0.9996, the R-squared value was 0.9991, and the adjusted R-squared value was 0.9990. The standard error was 1.362. For the 120% test, the R value was 0.9993, the R-squared value was 0.9986, and the adjusted R-squared value was 0.9984. The standard error was 1.7273. These results demonstrate that collection of the blood with additive at 100% of target ratios produces outstanding test results, and that deviation of up to 20% does not appreciably affect the quality of results. It should be noted that the experimental results for 20% are merely provided for comparison, and that a typical implementation of device 200 would include an error of no more than 5%.

Figure 16B:
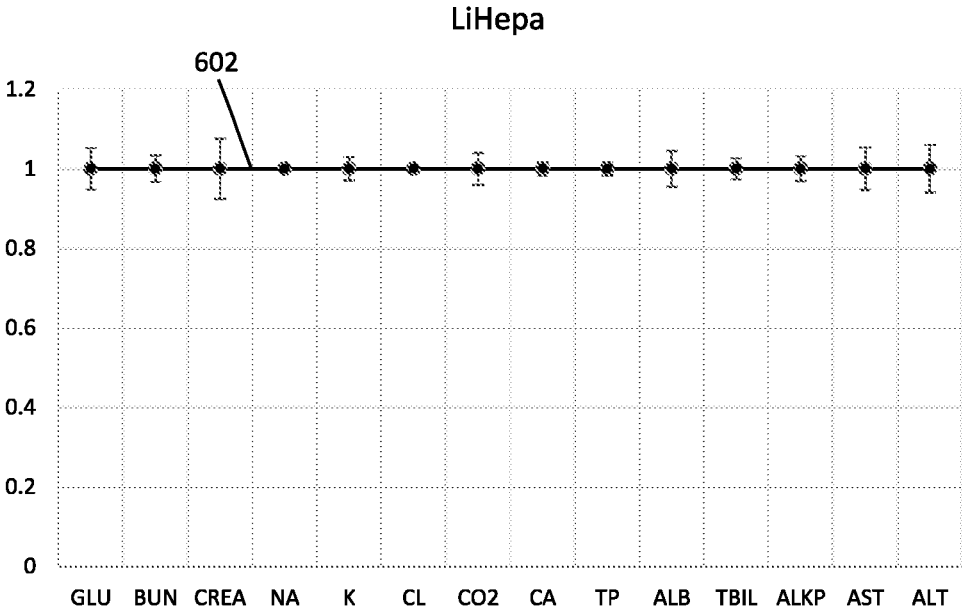

FIGS. 16A and 16B are normalized graphs for studies on blood samples obtained from six patients using the disclosed devices and methods. Graph 601 illustrates the normalized data points for six patients whose blood was mixed with EDTA, at both 80%, 100%, and 120%. The three measured outliers in the EDTA sample of FIG. 16A were all in the 80% tests. Graph 602 illustrates normalized data points for the same six patients whose blood was mixed with lithium heparin, again at 80%, 100%, and 120%. The results show that the results of the analyte tests are reproducible across multiple patients, with few outliers.

What is claimed is:
1. A blood collection tube, comprising:
a body including a proximal end and a distal end, and defining an axial extent between the proximal end and the distal end;
a chamber within the body;
a vacuum port at the distal end or along the axial extent; and a cap arranged on the proximal end, wherein the cap comprises:

a top face including a first septum;

a first conduit having an inlet extending from the first septum and an outlet in fluid communication with the chamber;

a lateral face including a second septum;

and a second conduit extending radially from the second septum and meeting the first conduit;

wherein, when a fluid source is fluidically connected to the first septum or the second septum, and a vacuum is applied at the vacuum port, the vacuum draws fluid from the fluid source, through the first or second septum, and into the first conduit.

2. The blood collection tube of claim 1, further comprising a passive mixing labyrinth arranged between the outlet of the first conduit and the chamber.

3. The blood collection tube of claim 2, wherein the passive mixing labyrinth is configured to mix fluid passing therethrough at least ten times before delivering the liquid to the chamber.

4. The blood collection tube of claim 2, wherein the passive mixing labyrinth comprises both lateral turns and axial turns.

5. The blood collection tube of claim 2, wherein the passive mixing labyrinth comprises a rupture disc axially aligned with the first conduit and the first septum.

6. The blood collection tube of claim 1, wherein the chamber has a funnel-shaped geometry including a conical portion at a proximal end thereof and a cylindrical portion at a distal end thereof.

7. The blood collection tube of claim 6, wherein an internal volume of the chamber is 1 ml, and a volume of the tube is between 3 ml and 5 ml.

8. The blood collection tube of claim 1, further comprising a membrane configured between the vacuum port and the chamber, said membrane configured to permit vacuum to be drawn therethrough but being non-permeable to liquid.

9. The blood collection tube of claim 8, further comprising a one-way valve between a distal end of the chamber and the membrane, said one-way valve configured to sequester collected fluid coming into contact with the membrane from fluid remaining in the chamber.

10. The blood collection tube of claim 1, wherein an axial length of the tube is between 75 and 100 mm, and a diameter of the cap is between 13 and 16 mm.

11. A device for collecting blood into the blood collection tube of claim 1, comprising:

a first slot for securing said blood collection tube therein;

a vacuum pump connectable to the vacuum port;

a second slot for securing a needle therein;

a plurality of conduits, each conduit connected at a distal end thereof to one of a plurality of reservoirs; and a processor configured to specify a predetermined volume of additive to be delivered into a blood collection tube from an additive reservoir belonging to the plurality of reservoirs and a predetermined volume of blood to be delivered into the blood collection tube via the needle;

wherein, the vacuum pump, plurality of conduits, and second slot are arranged around the first slot such that when the blood collection tube is inserted into the first slot:

the vacuum pump is configured to draw the vacuum through the vacuum port;

each conduit is fluidically connectable to an interior of the blood collection tube via the second septum; and a needle secured within the second slot is fluidically connectable to an interior of the blood collection tube via the first septum;

and the processor is configured to control the vacuum delivered from the vacuum pump so as to draw the predetermined volumes of additive and blood into the blood collection tube.

12. The device of claim 11, wherein each conduit comprises a needle that is separately insertable into and removable from the second septum.

13. The device of claim 12, further comprising a screw conveyor system for delivering each respective additive from a respective reservoir to the second septum, wherein each needle is a tip of a respective screw conveyor.

14. The device of claim 11, further comprising a valve configured between each conduit and respective reservoir, and a sensor array configured to monitor flow of additive through each valve, wherein, upon receipt of input specifying a volume of additive to be delivered from a particular reservoir, the processor directs opening of a corresponding valve, and when the sensor array senses that a specified volume of additive has entered the conduit from the reservoir, the processor directs closure of the corresponding valve.

15. The device of claim 11, wherein the second slot comprises a locking slot for securing the needle in the first septum.

16. The device of claim 15, further comprising a sensor arranged at the locking slot and configured to sense locking of the needle into the locking slot.

17. The device of claim 16, wherein, upon sensing of locking of the needle into the locking slot, the processor initiates a self-priming process.

18. The device of claim 11, further comprising a vacuum reservoir configured to store negative pressure from the vacuum pump.

19. The device of claim 11, further comprising a plurality of adhesive labels, a printer arranged to print on the plurality of adhesive labels, and a roller configured to rotate the blood collection tube within the first slot in order to apply a printed label onto an exterior of the blood collection tube.

20. The device of claim 11, further comprising a screen, wherein the processor is configured to display on the screen information regarding an identity of the patient from whom blood is to be collected, a volume of additive to add to the blood collection tube, and a quantity of blood to collect in the blood collection tube.

21. The device of claim 20, further comprising a scanner for scanning a bar code encoding patient information, and a memory containing stored patient information, wherein the processor is configured to permit collection of blood only when scanned encoded information matches the stored patient information.

22. The device of claim 21, further comprising a wireless transceiver configured to wirelessly receive and transmit the stored patient information.

23. The device of claim 11, wherein the device is hand-held.

24. A system for collecting blood, comprising the device of claim 11, and said blood collection tube.

* * * * *